United States Patent
Marks et al.

(10) Patent No.: US 9,228,056 B2
(45) Date of Patent: Jan. 5, 2016

(54) POLYMERS DERIVED FROM RENEWABLY RESOURCED LYSINOL

(71) Applicant: E I DU PONT DE NEMOURS AND COMPANY, Wilmington, DE (US)

(72) Inventors: David Neil Marks, Newark, DE (US); Kenneth Gene Moloy, Hockessin, DE (US); Mark A Scialdone, West Grove, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/337,440

(22) Filed: Jul. 22, 2014

(65) Prior Publication Data

US 2014/0329984 A1    Nov. 6, 2014

Related U.S. Application Data

(62) Division of application No. 13/835,313, filed on Mar. 15, 2013, now Pat. No. 8,933,189.

(51) Int. Cl.

| | |
|---|---|
| C08G 69/26 | (2006.01) |
| C08G 71/02 | (2006.01) |
| C08G 18/73 | (2006.01) |
| C08J 9/14 | (2006.01) |
| C08G 59/64 | (2006.01) |
| C08G 18/32 | (2006.01) |
| C08G 69/44 | (2006.01) |
| C08G 73/02 | (2006.01) |
| C08G 73/10 | (2006.01) |
| C08G 18/76 | (2006.01) |
| C07C 271/16 | (2006.01) |
| C08G 18/28 | (2006.01) |
| C08G 59/02 | (2006.01) |
| C08G 101/00 | (2006.01) |

(52) U.S. Cl.
CPC ............ *C08G 69/26* (2013.01); *C07C 271/16* (2013.01); *C08G 18/285* (2013.01); *C08G 18/3271* (2013.01); *C08G 18/73* (2013.01); *C08G 18/7671* (2013.01); *C08G 59/02* (2013.01); *C08G 59/64* (2013.01); *C08G 69/265* (2013.01); *C08G 69/44* (2013.01); *C08G 71/02* (2013.01); *C08G 73/0206* (2013.01); *C08G 73/10* (2013.01); *C08G 73/1075* (2013.01); *C08J 9/146* (2013.01); *C08G 2101/00* (2013.01); *C08G 2101/0025* (2013.01); *C08J 2375/02* (2013.01)

(58) Field of Classification Search
CPC .... C08G 18/73; C08G 59/64; C08G 18/3271; C08G 69/44; C08G 18/7671; C08G 18/285; C08G 69/265; C08G 69/26; C08G 18/603; C08G 73/14

See application file for complete search history.

(56) References Cited

U.S. PATENT DOCUMENTS

| 4,077,920 A | 3/1978 | Yukuta et al. |
| 5,068,311 A | 11/1991 | Horn et al. |

FOREIGN PATENT DOCUMENTS

| CN | 102617364 A | 8/2012 |
| EP | 0405239 A2 | 1/1991 |
| EP | 2341093 A1 | 7/2011 |
| JP | 52148036 A | 12/1977 |
| WO | 2006010278 A1 | 2/2006 |

OTHER PUBLICATIONS

International Search Report dated Jul. 28, 2014, International Application No. PCT/US2014/025251.
Kihara, Nobuhiro et al., Optically Active Poly(hydroxyurethane)s Derived From Cyclic Carbonate and L-Lysine Derivatives, Journal of Polymer Science, Part A: Polymer Chemistry, 1996, pp. 2173-2179, vol. 34.

*Primary Examiner* — Nathan M Nutter

(57) ABSTRACT

Disclosed are salt compositions of lysinol and dicarboxylic acids; and lysinol derived polymers including polyamide, polyimide, polyurea, cross-linked polyurea comprising urethane linkages, polyurea foams, cross-linked polyurea foams, and lysinol-epoxy thermoset.

12 Claims, No Drawings

POLYMERS DERIVED FROM RENEWABLY RESOURCED LYSINOL

FIELD OF THE INVENTION

The present invention relates to salt compositions of lysinol and dicarboxylic acids, and lysinol derived polymers including polyamide, polyimide, polyurea, polyurethane and lysinol-epoxy thermoset.

BACKGROUND OF THE INVENTION

The production of chemical products, chemical intermediates, monomers, and polymers is an important industry. The chemical industry supplies many of the raw materials and finished products that are in use today. Many of the components that are supplied by the chemical industry are produced using petroleum feedstocks as the initial source. Some of these components can be refined or otherwise purified directly from petroleum. Other components need to be subjected to further processes or chemical reactions to produce the desired products or intermediates.

With a growing world population, the demand for products produced by the chemical industry is increasing. This growing demand places a high burden on the petroleum feedstock, a non-renewable resource that is becoming increasingly costly to obtain due to diminishing resources.

A need exists to produce chemical products and chemical intermediates from resources other than petroleum. There have been attempts in the past to produce chemicals wherein at least part of the molecule is renewably resourced, i.e., is produced from non-petroleum or non-fossil carbon feedstock. Further, there is a need for polymers and materials derived from renewable resources. There is also a need for renewably sourced chemical products, chemical intermediates, monomers, and polymers containing nitrogen.

Lysine is an amino acid manufactured on very large scale by fermentation of sugars and other renewable carbon sources. Lysine and its derivatives, for example lysinol, are therefore potentially useful renewably resourced chemicals that are alternatives to nitrogen-containing, petroleum-derived chemicals.

Hence, there is a need for renewably sourced polymers derived from lysinol such as polyamide, polyimide, polyurea, polyurethane and lysinol-epoxy thermoset.

SUMMARY OF THE INVENTION

In an aspect of the present invention, there is a polyamide having the following structure:

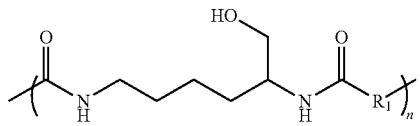

wherein $R^1$ is a substituted or unsubstituted alkyl or aryl group, and may be cyclic or acyclic; and
wherein the polyamide is derived from:
 (a) a diamine comprising lysinol and at least one of a dicarboxylic acid, a dicarboxylic acid ester, a diacid halide or a dinitrile; or
 (b) a salt comprising lysinol and a dicarboxylic acid, wherein the molar ratio of lysinol and the dicarboxylic acid is 1:1.

Another aspect of the present invention relates to a polyimide having the following structure:

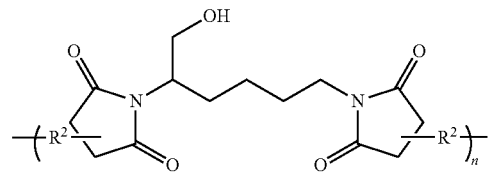

wherein $R^2$ is a substituted or unsubstituted alkyl and or aryl group, and may be cyclic or acyclic;
wherein n is large enough to provide a polyimide with molecular weight of at least 5,000; and
wherein the polyimide is derived from a diamine comprising lysinol and a dianhydride.

Another aspect of the present invention relates to a lysinol-epoxy thermoset having the following structure:

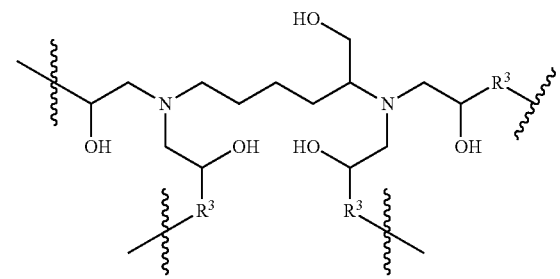

wherein $R^3$ is a substituted or unsubstituted alkyl and or aryl group, and may be cyclic or acyclic; and
wherein the lysinol-epoxy thermoset is derived from lysinol and an epoxy resin having at least two 1,2-epoxy groups per molecule.

Another aspect of the present invention relates to a polyurea having the following general structure:

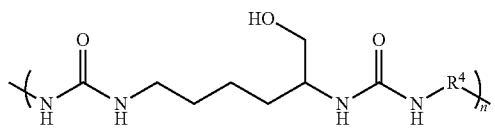

wherein $R^4$ is a substituted or unsubstituted alkyl and or aryl group, and may be cyclic or acyclic;
wherein n is sufficiently large to provide a polyurea with molecular weight of at least 5,000; and
wherein the polyurea is derived from a diamine comprising lysinol and a polyisocyanate, wherein the polyisocyanate comprises aliphatic polyisocyanate; alicyclic polyisocyanate; aroaliphatic polyisocyanate; aromatic polyisocyanate; or mixtures thereof.

In an aspect, the polyurea is a cross-linked polyurea comprising urethane linkages resulting from the reaction of isocyanate group of polyisocyanate with the alcohol group of lysinol.

In an aspect, there is a foam comprising:
 (a) a continuous polymeric phase defining a plurality of cells, wherein:
  the continuous polymeric phase comprises polyurea derived from lysinol and a polyisocyanate, wherein the polyisocyanate comprises aliphatic polyisocyanate, alicyclic polyisocyanate, aroaliphatic polyisocyanate, aromatic polyisocyanate; or mixtures thereof, the plurality of cells comprises a plurality of open-cells and a plurality of closed-cells; and (b) a discontinuous phase disposed in at least a portion of the plurality of closed-cells, the discontinuous phase comprising one or more blowing agents.

In another aspect, the foam is a cross-linked polyurea foam, wherein the polyurea is a cross-linked polyurea comprising urethane linkages resulting from the reaction of isocyanate group of the polyisocyanate with the alcohol group of lysinol.

In an aspect, enantioenriched (S)-lysinol or enantioenriched (L)-lysinol is prepared by hydrogenating enantiopure or enantioenriched lysine. In another aspect, the polymers derived from the enantiomerically enriched lysinol are optically active.

DETAILED DESCRIPTION

As used herein, the term (R)-Lysine is used interchangeably with (+)-Lysine and D-Lysine; the term (S)-Lysine is used interchangeably with (−)-Lysine and L-Lysine; (R)-Lysinol is used interchangeably with D-Lysinol; the term (S)-Lysinol is used interchangeably L-Lysinol; and the term "enantiomerically enriched (S)-lysinol" is used interchangeably with "enantioenriched (S)-lysinol", "enantiomerically enriched L-lysinol" and "enantioenriched L-lysinol". As used herein, the term "enantiopure lysine" is used interchangeably with "(S)-lysine" and "(R)-lysine". As used herein, the term "racemic lysine" is used interchangeably with a "equal ratio of (S)-lysine and (R)-lysine. As used herein, the term "dicarboxylic acid" is used interchangeably with "diacid".

As used herein, the term "biologically-derived" is used interchangeably with "bio-derived" and refers to chemical compounds including monomers and polymers, that are obtained from plants and contain only renewable carbon, and not fossil fuel-based or petroleum-based carbon. Hence, bio-derived materials have less impact on the environment as their creation does not deplete diminishing fossil fuels and, upon degradation, releases carbon back to the atmosphere for use by plants once again.

In an aspect, there is a process for the production of the enantioenriched (S)-lysinol with a ratio of (S)-lysinol to (R)-lysinol in the range of 99:1 to 51:49. The process comprising the steps of hydrogenating enantioenriched (S)-lysine in the presence of an aqueous acid and a hydrogenation catalyst, followed by treating the solution with a base, and finally distilling the (S)-lysinol as shown below in scheme 1:

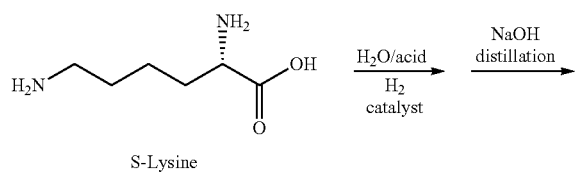

Scheme 1

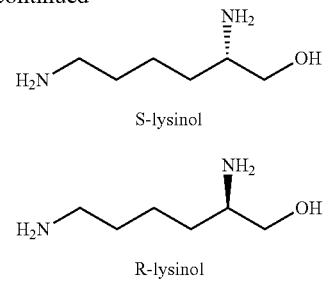

In an embodiment, the process as disclosed herein above is used in the preparation of enantioenriched (R)-lysinol with a ratio of (R)-lysinol to (S)-lysinol in the range of 99:1 to 51:49 from (R)-lysine. In another embodiment, the process as disclosed herein above is used in the preparation of racemic lysinol from racemic lysine. In another embodiment, the process as disclosed herein above is used in the preparation of racemic lysinol from enantioenriched (S)-lysine or enantioenriched (L)-lysine.

In particular, the process comprises charging a high pressure reactor with a solution of lysine in water, acid, and a hydrogenation catalyst. The high pressure reactor may be a batch, continuous, or semi-continuous reactor. The acid including, but not limited to sulfuric acid or phosphoric acid, is present in an amount of at least 0.5 molar equivalent of lysine or 1 molar equivalent or of lysine or 2 molar equivalent of lysine. Alternatively, the pH of the aqueous lysine solution can be adjusted with an acid to a pH in the range of 1-5 or 1.5-4 or 2-3. The catalyst is present in an amount in the range of 0.2-50% or 0.5-10% or 1-5% by weight of the total reaction mass. The hydrogenation catalyst can be chosen from those known in the art, for example ruthenium supported on carbon, platinum supported on carbon, platinum supported on titanium dioxide, or supported rhenium-ruthenium or rhenium-platinum catalysts. The process further comprises filling the reactor with hydrogen up to a pressure in the range of 0.7-14 MPa or 1.5-11 MPa or 2-9 MPa at a temperature in the range of 50-220° C. or 100-200° C. or 120-180° C. The process also comprises maintaining the pressure until ceasing of hydrogen uptake. The process further comprises cooling the reactor to room temperature and adding sodium hydroxide until pH is greater than 12. The process also comprises removing water and extracting the resulting residue, a mixture of lysinol and salt, with a solvent that will dissolve lysinol but not the salts and then removing the solvent to obtain lysinol in the form of a colorless oil. In an embodiment, the lysinol is enantioenriched (S)-lysinol. In another embodiment, the ratio of (S)-lysinol to (R)-lysinol is in the range of 99.9:0.1 to 51:49 or 98:2 to 70:30 or 95:5 to 80:20.

In an embodiment, lysinol (2,6-diamino-1-hexanol) is bio-derived lysinol, derived in one step from lysine, a chemical produced by fermentation of biomass.

In an aspect, there is a salt of lysinol and a dicarboxylic acid (HOOCR$^1$COOH), wherein the molar ratio of lysinol and the dicarboxylic acid is 1:1. In an embodiment, the lysinol is enantioenriched (S)-lysinol. In another embodiment, the ratio of (S)-lysinol to (R)-lysinol is in the range of 99:1 to 51:49 or 98:2 to 70:30 or 95:5 to 80:20.

Any suitable dicarboxylic acid (HOOCR$^1$COOH) such as an aliphatic diacid, an aromatic diacid or mixtures thereof can be used.

The aliphatic diacid (HOOCR$^1$COOH) may include from 21 to 18 carbon atoms in the main chain (R$^1$). Suitable aliphatic diacids include, but are not limited to, fumaric acid;

maleic acid; succinic acid; glutaric acid; adipic acid; pimelic acid; suberic acid; azelaic acid; sebacic acid; itaconic acid; malonic acid; mesaconic acid dodecanediacid; 1,12-dodecanedioic acid; 1,14-tetradecanedioic acid; 1,16-hexadecanedioic acid; 1,18-octadecanedioic acid; 1,2- or 1,3-cyclohexane dicarboxylic acid; and mixtures thereof.

An aromatic diacid (HOOCR$^1$COOH) may include a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, lower alkyl, lower alkoxy, lower alkylthio, trifluoromethyl, lower acyloxy, aryl, heteroaryl, and hydroxy. Suitable aromatic diacids include, but are not limited to, phthalic acid; isophthalic acid; p-(t-butyl)isophthalic acid; 1,2- or 1,3-phenylenediacetic acid; terephthalic acid; 2,5-dihydroxyterephthalic acid (DHTA); 4,4'-benzo-phenonedicarboxylic acid; 2,5 and 2,7-naphthalenedicarboxylic acid and mixtures thereof.

In an aspect, there is a polyamide having structure 1, derived from a diamine comprising lysinol and at least one of a dicarboxylic acid (HOOCR$^1$COOH), carboxylic acid ester (R'OR$^1$OR'), a diacid halide (XOCR$^1$COX) or a dinitrile (NCR$^1$CN), as shown in scheme 2:

Scheme 2

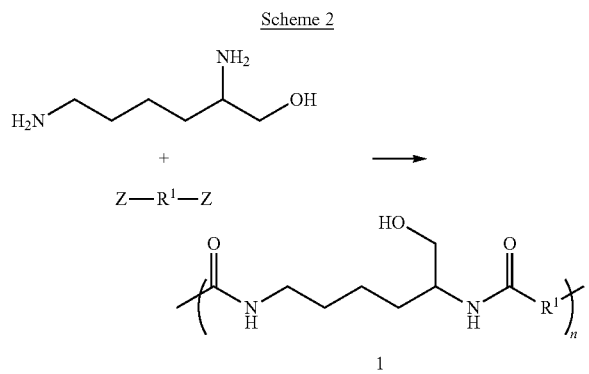

where Z is a carboxylic acid (—COOH), carboxylic acid ester (—COOR'), carboxylic acid halide (—COX), or nitrile group (—CN);

R$^1$ is any of a variety of aliphatic or aromatic groups, may be cyclic or acyclic; and may be combinations thereof; and n is sufficiently large to provide an average molecular weight of at least 5,000 and preferably greater than 15,000.

In an embodiment, the lysinol is an enantiomerically enriched (S)-lysinol. In some embodiments, the ratio of (S)-lysinol to (R)-lysinol is in the range of 99:1 to 51:49 or 98:2 to 70:30 or 95:5 to 80:20. In another embodiment, the polyamide is an optically active polyamide.

Optically active polymers provide potential usefulness relative to conventional polymers in applications such as separation and purification of chiral molecules, analytical and synthetic purposes, for instance drugs and pharmaceuticals, and as well as in optics applications.

In some embodiments, the diamine further comprises a diamine comonomer, wherein the diamine comonomer (H$_2$N-M-NH$_2$) is an aliphatic diamine, an aromatic diamine, or mixtures thereof, and the resulting polyamide is a copolymer having a general structure 2 as shown below in scheme 3:

Scheme 3

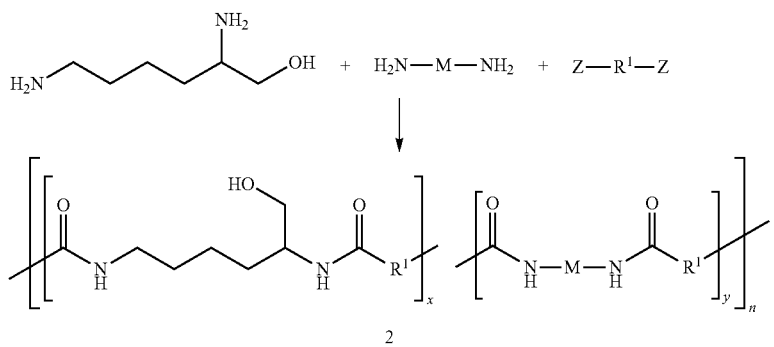

where R$^1$ and Z are as defined above;
M is a cyclic or acyclic aliphatic or aromatic group;
x can range from 0.01 to 1.0, y can range from 0 to 0.99, and x+y=1.0;
n is sufficiently large to provide an average molecular weight of at least 5,000 and preferably greater than 15,000.

Any suitable aliphatic diamine comonomer (H$_2$N-M-NH$_2$) can be used, such as those with 2 to 12 number of carbon atoms in the main chain. Suitable aliphatic diamines include, but are not limited to 1,2-ethylenediamine; 1,6-hexamethylenediamine; 1,5-pentamethylenediamine; 1,4-tetramethylenediamine; bis(aminomethyl)cyclohexane; 5-amino-1,3,3-trimethyl cyclohexanemethanamine; 1,12-dodecanediamine; and mixtures thereof.

Any suitable aromatic diamine comonomer (H$_2$N-M-NH$_2$), such as those with ring sizes between 6 and 10 can be used. Suitable aromatic diamines include, but are not limited to m-xylylenediamine; p-phenylenediamine; 3,3'-dimethylbenzidine; 2,6-naphthylenediamine; 4,4'-diaminodiphenyl ether; 4,4'-diaminodiphenyl sulfone; 1,12-dodecanediamine and mixtures thereof.

The molar ratio of lysinol to diamine comonomers (H$_2$N-M-NH$_2$) in the polyamide is in the range of 100:0 to 5:95 or 50:50 to 20:80 or 10:90 to 1:99. The molar ratio of at least one of a dicarboxylic acid, a diacid halide or a dinitrile to the total molar amount of lysinol and diamine comonomer in the polyamide is in the range of 0.9:1.1 to 0.95:1.05 or 0.99:1.01.

In an embodiment, the polyamide 1 is derived from a diamine comprising lysinol and a dicarboxylic acid (HOOCR¹COOH) as shown below in scheme 4:

Scheme 4

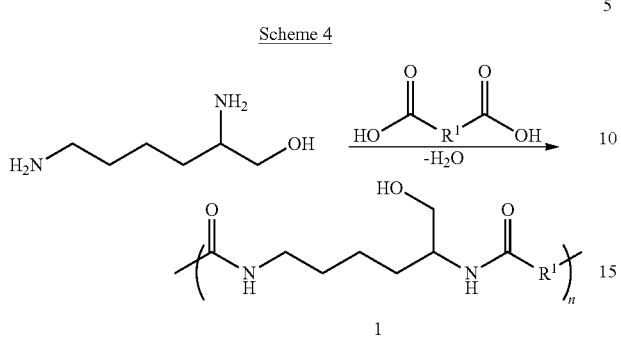

where R¹=substituted or unsubstituted alkyl or aryl group and may be cyclic or acyclic; and n is sufficiently large to provide an average molecular weight of at least 5,000 and preferably greater than 15,000.

Any suitable dicarboxylic acid (HOOCR¹COOH), as disclosed supra, such as an aliphatic diacid, an aromatic diacid, cycloaliphatic diacid and mixtures thereof can be used.

In an embodiment, the polyamide 1 is derived from a diamine comprising lysinol and a derivative of dicarboxylic acid, such as diester (R'OOCR¹COOR'), as shown below in scheme 5:

Scheme 5

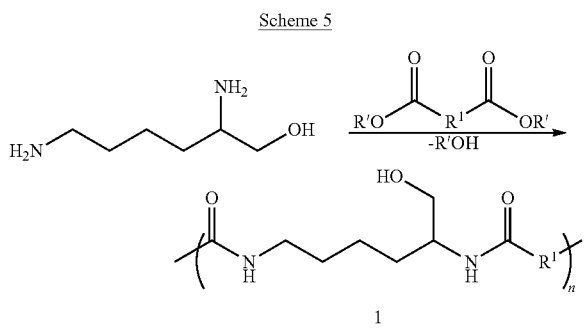

R' = alkyl, aryl where R¹=substituted or unsubstituted alkyl or aryl group; and n is sufficiently large to provide an average molecular weight of at least 5,000 and preferably greater than 15,000.

Suitable esters (R'OOCR¹COOR') of dicarboxylic acids (HOOCR¹COOH) described supra include, but are not limited to, methyl, ethyl, isopropyl, n-propyl, n-butyl, isobutyl, sec-butyl or tert-butyl esters, more preferably the methyl, ethyl or n-butyl esters.

In an embodiment, diacids and their esters are obtained from renewable sources, such as azelaic acid, sebacic acid, succinic acid, and mixtures thereof. In one embodiment, the polyamide is bio-derived or substantially bio-derived with the total content of bio-derived diacid in the range of 10-95% or 15-80% or 20-60% or 25-50% by moles with respect to the total molar content of the diacids and their esters in the polyamide.

In another embodiment, the polyamide 1 is derived from a diamine comprising lysinol and a diacid halide (XOCR¹COX), as shown below in scheme 6:

Scheme 6

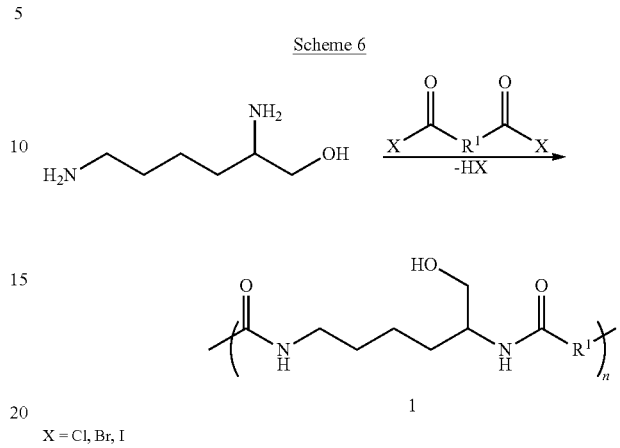

X = Cl, Br, I where R¹=substituted or unsubstituted alkyl or aryl group and may be cyclic or acyclic; and n is sufficiently large to provide an average molecular weight of at least 5,000 and preferably greater than 15,000.

Suitable aliphatic diacid halides (XCOR¹COX), include, but are not limited to butylene diacid chloride; butylene diacid bromide; hexamethylene diacid chloride; hexamethylene diacid bromide; octamethylene diacid chloride; octamethylene diacid bromide; decamethylene diacid chloride; decamethylene diacid bromide; dodecamethylene diacid chloride; dodecamethylene diacid bromide; and mixtures thereof. Suitable aromatic diacid halide include, but are not limited to terephthaloyl dichloride; 4,4'-benzoyl dichloride; 2,6-naphthalenedicarboxyl acid dichloride; 1,5-naphthalene dicarboxyl acid dichloride; tolyl diacid chloride; tolylmethylene diacid bromide; isophorone diacid chloride; isophorone diacid bromide; 4,4'-methylenebis(phenyl acid chloride); 4,4'-methylenebis(phenyl acid bromide); 4,4'-methylenebis (cyclohexyl acid chloride); 4,4'-methylenebis(cyclohexyl acid bromide) and mixtures thereof.

In another embodiment, the polyamide 1 is derived from a diamine comprising lysinol and a dinitrile (NCR¹CN), as shown below in scheme 7:

Scheme 7

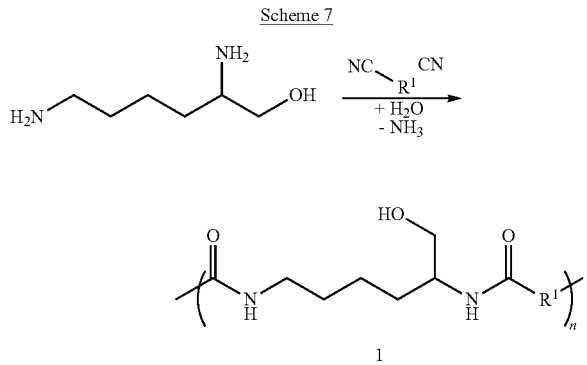

where R¹=substituted or unsubstituted alkyl or aryl group and may be cyclic or acyclic; and n is sufficiently large to provide an average molecular weight of at least 5,000 and preferably greater than 15,000.

Suitable dinitrile compounds (NCR¹CN) include, but are not limited to methylglutaronitrile; ethylsuccino-nitrile; adiponitrile; fumarodinitrile; succinodinitrile; 3-hexenoic acid dinitrile; octanoic acid dinitrile; decanoic acid dinitrile; 1,5-dicyanopentane; 1,6-dicyanohexane; 1,7-dicyanoheptane; 1,8-dicyanooctane; 1,9-dicyanononane; 1,10-dicyanodecane; phthalonitrile; isophthalonitrile; terephthalonitrile; and mixtures thereof.

In an embodiment, the polyamide 1 is derived from a salt comprising lysinol and a dicarboxylic acid, wherein the molar ratio of lysinol and the dicarboxylic acid is 1:1. It is well known in the art that 1:1 diamine:diacid salts provide a means to control stoichiometry and to provide high molecular weight in step growth polymerizations such as that used to prepare polyamides.

The number average molecular weight of the polyamide derived from lysinol is at least 5,000, or at least 10,000, or at least 15,000 or higher.

In an embodiment, the polyamide is at least 20% or 40% or 60%, and preferably 100% bio-derived. Examples of 100% bio-derived polyamides derived from lysinol are poly(lysinol/sebacic acid), poly(lysinol/succinic acid), and poly(lysinol/2,5-furancarboxylic acid).

In another embodiment, the polyamides having structures 1 and 2 are partially crosslinked through the formation of ester and amide groups between lysinol and the other monomer comprising dicarboxylic acid, dicarboxylic ester, dicarboxylic halide, or dinitrile, as shown below in Scheme 8:

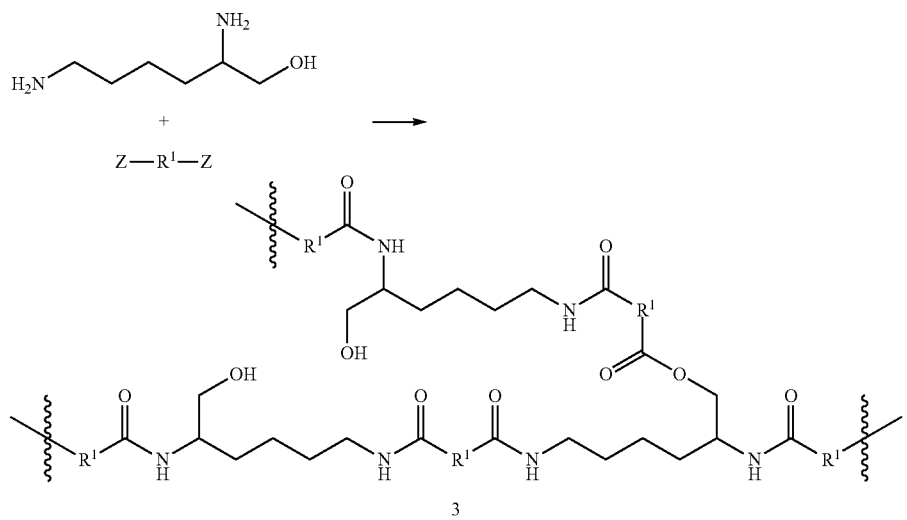

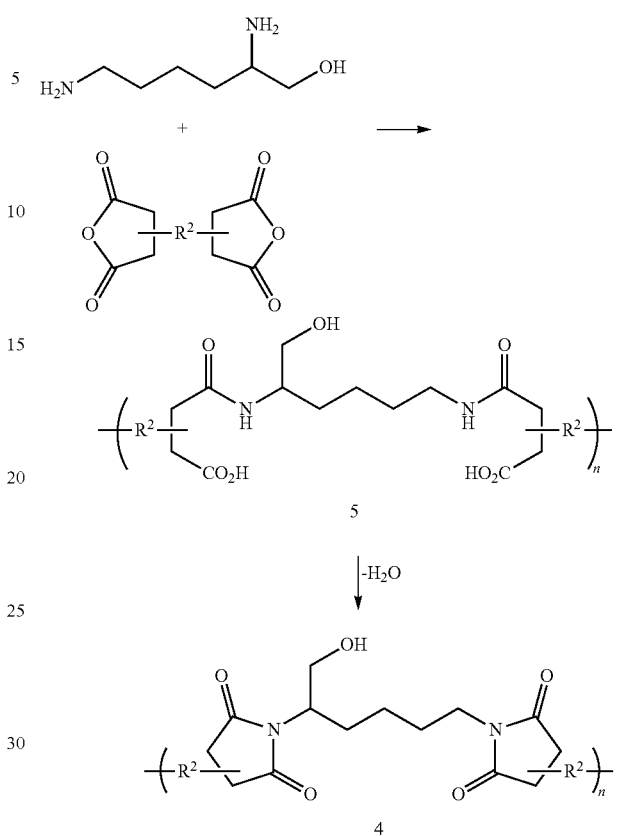

where Z=carboxylic acid (CO₂H), carboxylic ester (CO₂R'; R' as previously defined), a carboxylic halide (COCl, COBr, COI), or nitrile (CN); and R¹=substituted or unsubstituted alkyl or aryl group, and may be cyclic or acyclic as previously defined.

In an aspect, there is a polyimide 4 is derived from a diamine comprising lysinol and a dianhydride as shown below in Scheme 9:

where R²=an aliphatic group, an aromatic group, or a combination of aliphatic and aromatic groups linking two cyclic anhydride groups; R² may be cyclic or acyclic; and R² may be optionally substituted with oxygen-, sulfur-, halogen-, or nitrogen-containing groups; and n is sufficiently large to provide an average molecular weight of at least 5,000 and preferably greater than 15,000.

Suitable dianhydrides

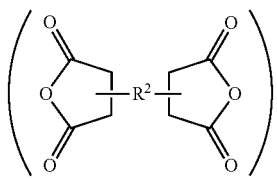

include, but are not limited to pyromellitic dianhydride (PMDA); biphenyltetracarboxylic dianhydlride (BPDA); benzophenonetetracarboxylic acid dianhydride; cyclopentanetetracarboxylic dianhydride; diphenyl sulphone tetracarboxylic dianhydride; 5-(2,5-dioxotetrahydro-3-furanyl)-3-methyl-3-cyclohexene-1,2-dicarboxylic dianhydride; bis(3,4-dicarboxyphenyl)ether dianhydride; bis(3,4-dicarboxyphenyl)thioether dianhydride; bisphenol-A bisether dianhydride; 2,2-bis(3,4-dicarboxyphenyl) hexafluoropropane dianhydride; 2,3,6,7-naphthalenetetracarboxylic acid dianhydride; bis(3,4-dicarboxyphenyl)sulphone dianhydride; 1,2,5,6-naphthalenetetracarboxylic dianhydride; 2,2',3,3'-biphenyltetracarboxylic dianhydride; hydroquinone bisether dianhydride; 3,4,9,10-perylene tetracarboxylic dianhydride; 1,2,3,4-cyclobutanetetracarboxylic dianhydride; 3,4-dicarboxy-1,2,3,4-tetrahydro-1 naphthalene-succinic dianhydride; bicyclo(2,2)oct-7-ene-2,3,5,6-tetracarboxylic dianhydride; tetrahydrofuran-2,3,4,5-tetracarboxylic dianhydride; 2,2-bis(3,4dicarboxyphenyl)propane dianhydride; 3,3',4,4'-biphenyltetracarboxylic dianhydride (BPDA); 4,4'-oxydiphthalic dianhydride (ODPA); ethylenediamine tetraacetic acid dianhydride (EDTAh) and mixtures thereof. In an embodiment, the anhydride is an oligomer or a polymer containing at least one anhydride functional group.

The polyimide 4 in accordance with the present invention can be prepared from the copolymerization of lysinol and dianhydride(s)

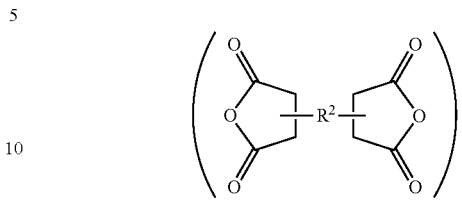

to first give a polyamic acid 5, as shown in Scheme 9, which is subsequently converted to the polyimide 4.

In an embodiment, the diamine in the polyimide 4 further comprises a diamine comonomer ($H_2N$-M-$NH_2$) disclosed supra and the polyimide is a polyimide copolymer 6 as shown below in scheme 10:

Scheme 10

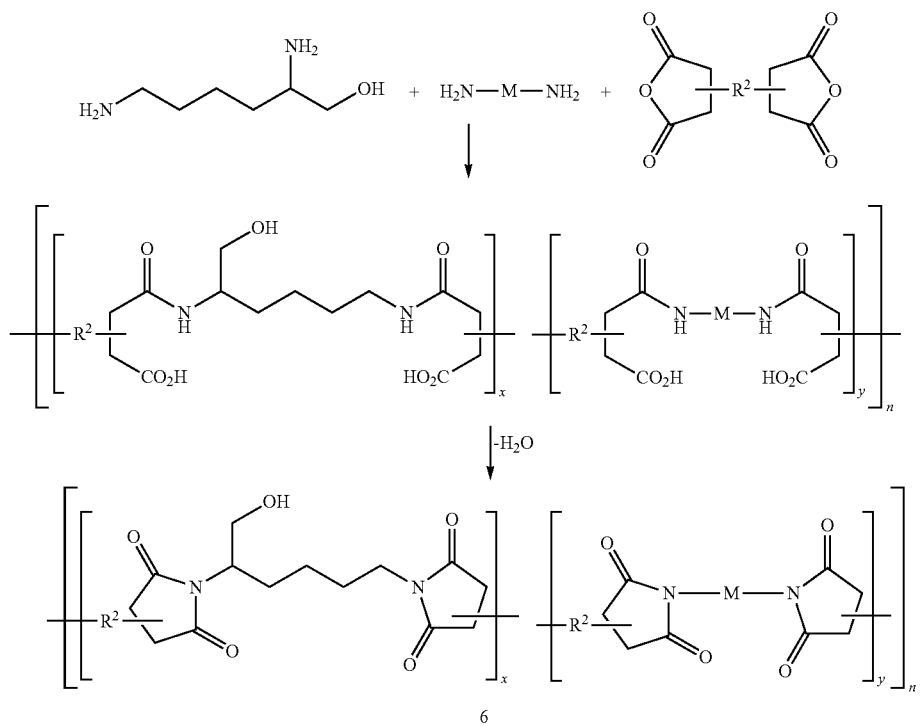

where $R^2$=an aliphatic group, an aromatic group, or a combination of aliphatic and aromatic groups linking two cyclic anhydride groups; $R^2$ may be cyclic or acyclic; and $R^2$ may be optionally substituted with oxygen-, sulfur-, halogen-, or nitrogen-containing groups;

M is a cyclic or acyclic aliphatic or aromatic group;

x can range from 0.01 to 1.0, y can range from 0 to 0.99, and x+y=1.0; and n is sufficiently large to provide an average molecular weight of at least 5,000 and preferably greater than 15,000.

In an embodiment, the lysinol is enantiomerically enriched (S)-lysinol described supra and the polyimide is an optically active polyimide.

The molar ratio of the dianhydride to the total molar amount of lysinol and diamine comonomers in the polyimides 4 and 6 is in the range of 0.9 to 1.1, or 0.95 to 1.05, or 0.99 to 1.01. The molar ratio of lysinol to diamine comonomers in the polyamide is 100:0 to 5:95 or 50:50 to 20:80 or 10:90 to 1:99.

In an aspect, there is a lysinol-epoxy thermoset 7 derived from lysinol and an epoxy resin, as shown below in scheme 11:

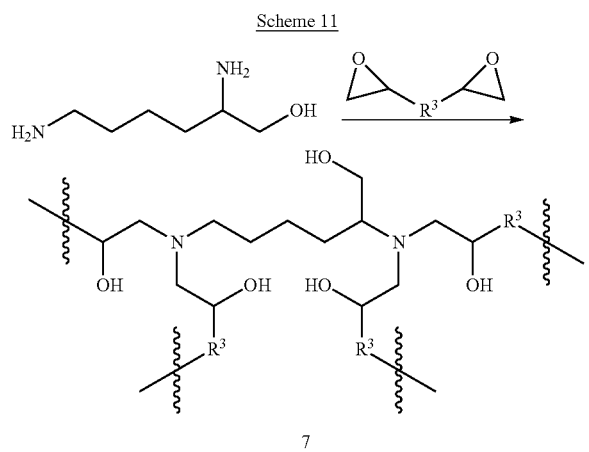

where $R^3$ is substituted or unsubstituted alkyl or aryl group. and where the lysinol-epoxy thermoset 7 is crosslinked by multiple addition reactions occurring at each nitrogen atom in the lysinol monomer In an embodiment, the lysinol is enantiomerically enriched (S)-lysinol described supra and the lysinol-epoxy thermoset 7 is an optically active lysinol-epoxy thermoset.

The epoxy resin comprises at least two 1,2-epoxy groups per molecule and can be a monomer, an oligomer, or a polymer. The epoxy resin can have molecular weight in the range of 130-10,000 or 250-5000 or 300-2000 with two or more epoxy groups per molecule.

Suitable epoxy resins include, but are not limited to diethylene glycol diglycidyl ether; polyethylene glycol diglycidyl ether; glycerol polyglycidyl ether; diglycerol polyglycidyl ether; 1,2-epoxybutane; polyglycerol polyglycidyl ether; isoprene diepoxide; cycloaliphatic diepoxide; 1,4-cyclohexanedimethanol diglycidyl ether; glycidyl 2-methylphenyl ether; glycerol propoxylate triglycidyl ether; 1,4-butanediol diglycidyl ether; sorbitol polyglycidyl ether; glycerol diglycidyl ether; tetraglycidyl ether of meta-xylenediamine; diglycidyl ether of bisphenol A, bisphenol A diglycidyl ether; bisphenol A diglycidyl ether oligomers, phenol epoxy novolac; cresol epoxy novolac; triglycidylisocyanurate; 3',4'-epoxycyclohexylmethyl-3,4-epoxycyclohexanecarboxylate; 3,4-epoxycyclohexyloxirane; bis(3,4-epoxycyclohexylmethyl)adipate; epoxidized oils such as epoxidized soybean oil; and mixtures thereof.

The molar ratio of epoxy groups in the epoxy resin to lysinol in the lysinol-epoxy thermoset is in the range of 8:1 to 6:1 to 4:1 to 2:1.

The lysinol-epoxy thermoset in this invention can be prepared by mixing lysinol and epoxy resin and optionally heating the mixture to give a solid lysinol-epoxy thermoset.

In another aspect there is a polyurea having structure 8 derived from a diamine comprising lysinol and a polyisocyanate, as shown below in scheme 8. In another aspect, the polyurea is a cross-linked polyurea having structure 9, as shown below in scheme 8, comprising urethane linkages resulting from the reaction of isocyanate group of polyisocyanate with the alcohol group of lysinol, as shown below in scheme 8:

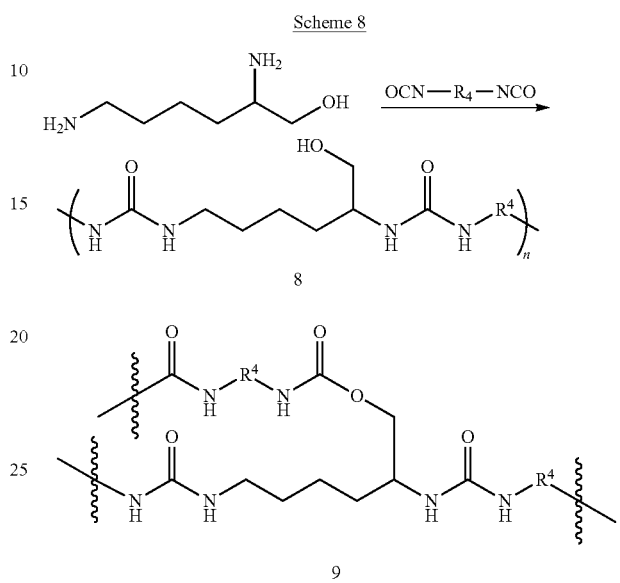

where $R^4$ is substituted or unsubstituted alkyl or aryl group and may be cyclic or acyclic.

In various embodiment, the relative amounts of polyurea and cross-linked polyurea can controlled by various factors, including but not limited to, stoichiometric amounts of lysinol and polyisocyanate; amount and nature of catalyst used in the reaction.

In an embodiment, the lysinol is enantiomerically enriched (S)-lysinol described supra and the polyurea is an optically active polyurea.

The polyisocyanate used herein are those isocyanates having a functionality of at least two, i.e. two isocyanate groups per molecule. Exemplary polyisocyanates include aliphatic polyisocyanates, alicyclic polyisocyanates, aroaliphatic polyisocyanates, and aromatic polyisocyanates as well as derivatives of these polyisocyanates. They can be used singly or in combination of two or more thereof.

Suitable aliphatic polyisocyanates include, but are not limited to trimethylene diisocyanate; tetramethylene diisocyanate; hexamethylene diisocyanate; pentamethylene diisocyanate; 1,2-propylene diisocyanate; 1,2-butylene diisocyanate; 2,3-butylene diisocyanate; 1,3-butylene diisocyanate; 2,4,4- or 2,2,4-trimethylhexamethylene diisocyanate; methyl 2,6-diisocyanatohexanoate (common name: lysine diisocyanate); 2-isocyanatoethyl 2,6-diisocyanatohexanoate; 1,6-diisocyanato-3-isocyanatomethylhexane; 1,4,8-triisocyanatooctane; 1,6,11-triisocyanatoundecane; 1,8-diisocyanato-4-isocyanatomethyloctane; 1,3,6-triisocyanatohexane; 2,5,7-trimethyl-1,8-diisocyanato-5-isocyanatomethyloctane; and mixtures thereof.

Suitable alicyclic polyisocyanates include, but are not limited to 1,3-cyclopentene diisocyanate; 1,4-cyclohexene diisocyanate; 1,3-cyclohexene diisocyanate; 3-isocyanatomethyl-3,5,5-trimethylcyclohexyl isocyanate (common name: isophorone diisocyanate); methyl-2,4-cyclohexene diisocyanate, methyl-2,6-cyclohexene diisocyanate; 1,3- or 1,4-bis (isocyanatomethyl)cyclohexane (hydrogenated xylylene diisocyanate); methylenebis(1,4-cyclohexanediyl)diisocyanate (hydrogenated MDI); and norbornane diisocyanate as well as alicyclic triisocyanates such as 1,3,5-triisocyanatocyclohexane; 1,3,5-trimethylisocyanatocyclohexane; 2-(3-isocyanatopropyl)-2,5-di(isocyanatomethyl)-bicyclo(2.2.1) heptane; 2-(3-isocyanatopropyl)-2,6-di(isocyanatomethyl)-bicyclo(2.2.1)heptane; 3-(3-isocyanatopropyl)-2,5-di(isocyanatomethyl)-bicyclo(2.2.1)heptane; 5-(2-isocyanatoethyl)-2-isocyanatomethyl-3-(3-isocyanatopropyl)-bicyclo(2-.2.1)heptane; 6-(2-isocyanatoethyl)-2-isocyanatomethyl-3-(3-isocyanatopropyl)-bicyclo(2-.2.1)heptane; 5-(2-isocyanatoethyl)-2-isocyanatomethyl-2-(3-isocyanatopropyl)-bicyclo(2-.2.1)heptane; and 6-(2-isocyanatoethyl)-2-isocyanatomethyl-2-(3-isocyanatopropyl)-bicyclo(2-.2.1)heptane.

Suitable aroaliphatic polyisocyanates include, but are not limited to methylenebis(1,4-phenylene)diisocyanate (MDI); 1,3- or 1,4-xylylene; diisocyanato-1,4-diethylbenzene; 1,3- or 1,4-bis(1-isocyanato-1-methylethyl)benzene (common name: tetramethylxylylene diisocyanate); 1,3,5-triisocyanatomethylbenzene; and mixtures thereof.

Suitable aromatic polyisocyanates include, but are not limited to m-phenylene diisocyanate; p-phenylene diisocyanate; 4,4'-diphenylene diisocyanate; 1,5-naphthalene diisocyanate; 2,4- or 2,6-tolylene diisocyanate; 4,4'-toluidine diisocyanate; 4,4'-diphenyl ether diisocyanate; triphenylmethane-4,4',4"-triisocyanate; 1,3,5-triisocyanatobenzene; 2,4,6-triisocyanatotoluene; 4,4'-diphenylmethane-2,2',5,5'-tetraisocyanate; and mixtures thereof.

The molar ratio of the sum of the reactive isocyanate functional groups in the polyisocyanates to lysinol in the polyurea is 1.5:1 or 2:1 or 3:1.

The polyurea, as disclosed herein can be prepared by mixing lysinol as a crosslinking agent and the polyisocyanate with stirring and optionally with additional ingredients such as solvents and foam blowing agents.

In coatings applications it is advantageous to have monomer and polymer systems with a plurality of polymerizable functional groups. Coating in general is a two step process. In the first step, a liquid or soluble polymer is prepared and coated onto a substrate. The liquid or soluble polymer is designed to have a control over properties, such as viscosity or wetting characteristics, that are important in forming a good coating. In a second step, the coating is cured by crosslinking the polymer. This approach is often used in the preparation of polyurethane and other types of coatings. Lysinol provides two amine and one alcohol functional groups. Amines are known to react rapidly with isocyanates to give urea linkages. Alcohols react with isocyanates to give urethane linkages. While not bound by any theory, it is believed that the reaction of isocyanates with alcohol groups of lysinol is much slower than with amine groups of lysinol and requires use of catalysts or high temperature. Hence formation of urethane linkages in a polyurea derived from lysinol and polyisocyanate can be used as a curing step of forming a polyurea/polyurethane coating.

A method of coating comprising coating a substrate with a coating medium comprising polyurea to form a polyurea coating, wherein the polyurea 8 is derived from a diamine comprising lysinol and a polyisocyanate, as shown above in scheme 12 and comprises urea linkages resulting from the reaction of isocyanate group of the polyisocyanate with the amine group of lysinol. The method of coating further comprising curing the polyurea coating to form a cross-linked polyurea coating, wherein the cross-linked polyurea coating comprises urethane linkages resulting from the reaction of isocyanate group of the polyisocyanate with the alcohol group of lysinol. In an embodiment, the coating medium is a solution comprising polyurea and a solvent. In another embodiment, the coating medium is a liquid polyurea, where polyurea is heated to a temperature above Tg to make it flowable.

In an aspect, there is a foam comprising a continuous polymeric phase defining a plurality of cells, wherein the continuous polymeric phase comprises polyurea derived from lysinol and a polyisocyanate, wherein the polyisocyanate comprises aliphatic polyisocyanate, alicyclic polyisocyanate, aroaliphatic polyisocyanate, aromatic polyisocyanate; or mixtures thereof, and wherein the plurality of cells comprises a plurality of open-cells and a plurality of closed-cells. The foam also comprises a discontinuous phase disposed in at least a portion of the plurality of closed-cells, the discontinuous phase comprising one or more blowing agents.

As used herein, the term "open-cell" refers to individual cells that are ruptured or open or interconnected producing a porous "sponge" foam, where the gas phase can move around from cell to cell. As used herein, the term "closed-cell" refers to individual cells that are discrete, i.e. each closed-cell is enclosed by polymeric sidewalls that minimize the flow of a gas phase from cell to cell. It should be noted that the gas phase may be dissolved in the polymer phase besides being trapped inside the closed-cell. Furthermore, the gas composition of the closed-cell foam at the moment of manufacture does not necessarily correspond to the equilibrium gas composition after aging or sustained use. Thus, the gas in a closed-cell foam frequently exhibits compositional changes as the foam ages leading to such known phenomenon as increase in thermal conductivity or loss of insulation value.

In another aspect, the foam is a polyurea foam, wherein the polymer comprises urea linkages resulting from the reaction of isocyanate group of the polyisocyanate with the amine group of lysinol.

In another aspect, the foam is a cross-linked polyurea foam, wherein the polyurea comprises cross-linked polyurea comprising urethane linkages resulting from the reaction of isocyanate group of the polyisocyanate with the alcohol group of lysinol.

In a typical foam preparation as practiced by those skilled in the art, a di- or polyisocyanate is combined with a di- or polyfunctional monomer containing alcohol or amine groups at about 0-30° C. The heat of the polymerization reaction causes the blowing agent to expand and results in foaming. A permanent foamed polymer structure is thus produced when the polymerization reaction is completed.

Suitable blowing agents include, but are not limited to carbon dioxide; hydrocarbons such as pentane, isopentane, cyclopentane petroleum ether, and ether; hydrochlorofluorocarbons such as 1,1-dichloro-1-fluoroethane (HCFC-141b); 2,2-dichloro-1,1,1-trifluoroethane (HCFC-123); 1-chloro-1,1-difluoroethane (HCFC-142b); 1,1,1,2-tetrafluoroethane (HCFC-134a); 1,1,1,3,3-pentafluoropropane (HFC-245fa) available from Honeywell (Morristown, N.J.); 1,1,1,3,3-pentafluorobutane (HFC-365) available as Solkane® 365mfc from Solvay Chemicals (Bruxelles, Belgium); incompletely halogenated hydrocarbons such as 2-chloropropane; fluorocarbons such as dichlorodifluoromethane, 1,2-dichloro-1,1,2,2-tetrafluoroethane (CFC-114), trichlorotrifluoroethane (CFC-113), trichloromonofluoromethane (CFC-11), 1,1,1,4,4,4-hexafluoro-2-butene, or mixtures thereof. The amount of blowing agent is in the range of 1-40%, or 5-20%, or 10-30%, by weight, based on the total weight of the pre-foam mixture.

The foams typically contain foam stabilizers and surfactants to control the foam cell structure as known to those skilled in the art in the range of 0.5-10%, or 2-8%, or 3-6%, by weight, based on the total weight of the pre-foam mixture. The surfactant is added to lower the surface tension and stabilize the foam cells during foaming and curing. The surfactant is at least one of ionic or non-ionic surfactants, including polymeric surfactants. A class of suitable surfactants includes siloxane-oxyalkylene copolymers such as those containing Si—O—C as well as Si—C linkages. The siloxane-oxyalkylene copolymers can be block copolymers or random copolymers. Typical siloxane-oxyalkylene copolymers contain a siloxane moiety composed of recurring dimethylsiloxy units endblocked with mononethylsiloxy and/or trimethylsiloxy units and at least one polyoxyalkylene chain composed of oxyethylene and/or oxypropylene units capped with an organic group such as an ethyl group. Suitable siloxane-oxyalkylene copolymeric surfactants include, but are not limited to, polyether-modified polysiloxanes, available as Tegostab B8406 from Evonik Goldschmidt Corporation (Hopewell, Va.); (polyalkyleneoxide modified heptamethyltrisiloxane available as Silwet L-77 from OSi Specialties (Danbury Conn.).

Another class of suitable surfactants includes silicone surfactants such as, L-7003, L-5350, L-5420, and L-5340 silicone surfactants, all available from Union Carbide Corporation, DC 193 available from Dow Chemical Co. (Midland, Mich.), and SF™ 1188 silicone surfactant available from GE Bayer Silicones.

Another class of suitable surfactants includes non-ionic organic surfactants such as the condensation products of alkylene oxides such as ethylene oxide, propylene oxide or mixtures thereof, and alkylphenols such as nonylphenol, dodecylphenol and the like. Suitable non-ionic organic surfactants include, but are not limited to, polysorbate (Tween®) surfactant, for example Tween® 20, Tween® 21, Tween® 61, Tween® 80 or Tween® 81 all available from Aldrich Chemical Company; Pluronic® non-ionic surfactants available from BASF Corp., (Florham Park, N.J.); Tergitol™; Brij® 98, Brij® 30, and Triton X 100, all available from Aldrich Chemical Company; and Merpol®LF available from E. I. du Pont de Nemours and Company (Wilmington Del.). Suitable ionic surfactant includes, but is not limited to sodium dodecylsulfonate (SDS).

The foam may optionally contain flame retardants in an amount of 1-15 wt %, and typically 2-10% by weight.

The lysinol-derived polymers as disclosed herein above, polyamide, polyimide, epoxy thermosets, polyureas and polyurea/polyurethanes described in this invention have a diverse range of potential applications, for example as coatings, coating primers, printed circuit boards, semiconductor encapsulants, tapes and adhesives, bonding materials, flexible foams, and rigid foams. Because lysine is manufactured by the fermentation of sugars and other biomass, the lysinol-derived polymers provide an especial advantage in that the amine monomer is not derived from petroleum and is renewably sourced. This reduced dependence on fossil petroleum provides a sustainable and cost-effective alternative to materials useful for these applications.

EXAMPLES

Materials and Methods

All solvents and reagents, unless otherwise indicated, were purchased from Sigma-Aldrich and used directly as supplied. Small scale high pressure reactions were conducted in a custom designed and constructed Hastelloy C vessel. The vessel was stirred magnetically. Reaction progress was monitored by pressure drop using a Setra Systems Model 206 Pressure Transducer (0-2000 psig range) and digital readout. $^1$H and $^{13}$C NMR spectra were recorded on a Brucker DRX 400 or 500 Spectrometer. Chemical shifts are reported in ppm relative to an internal reference.

Example 1

Preparation of Lysinol from Lysine Hydrogenation

The examples below illustrate the preparation of lysinol from the hydrogenation of lysine in the presence of a catalyst, hydrogen, and aqueous acid.

Example 1.1

Preparation of Lysinol (Lysinol-1.1) by Lysine Hydrogenation Using Phosphoric Acid A high pressure reactor was charged with 3.03 g lysine (20.7 mmol), 0.255 g (0.13 mmol Ru) Ru/C catalyst, and 17 mL of 2.53 M $H_3PO_4$ (43.0 mmol). After purging with hydrogen the reactor was brought to 6.9 MPa initial pressure at 120° C. and gas uptake was monitored. The vessel was repressurized to 6.9 MPa after 5.5 h and 20.5 h. Gas uptake ceased after ca. 24 h. After cooling and venting the reactor, a sample taken from the reactor showed complete lysine conversion by liquid chromatography. The slurry from the reactor was filtered and washed with water. NaOH (5.2 g, 130 mmol) dissolved in a minimal amount of water was added to the filtrate to get a solution with pH>12. Water was then removed from the solution on a rotary evaporator to provide a mixture of lysinol and sodium phosphate. This colorless residue was extracted with ethanol to separate the ethanol-soluble lysinol from the salt. The ethanol was removed on a rotary evaporator and the product, a colorless oil, was dried on a vacuum line to constant mass to get final product, lysinol (Lysinol-1.1) (2.98 g). Gas chromatography analysis of the Lysinol-1.1 showed 93 wt % lysinol.

Example 1.2

Preparation of Lysinol (Lysinol-1.2) by Lysine Hydrogenation Using Sulfuric Acid A 1 gallon plastic jug, cooled with a wet ice/acetone bath was charged with (S)-lysine (97%, 420.0 g, 2.79 mol) and 2.2 L of deionized water. Concentrated sulfuric acid (160 mL, 2.94 mol) was slowly added to the chilled slurry of (S)-lysine and water with stirring, maintaining the temperature below 30° C. The mixture was stirred until all of the lysine had dissolved and the temperature had returned to 20-25° C. The solution along with catalyst, 100.0 g of 5% ruthenium on carbon were then transferred to a one gallon autoclave reactor. The reactor was then pressurized with hydrogen to 6.9 MPa and heated to 120° C. Hydrogen was added as needed to the reactor to maintain 6.9 MPa pressure until the hydrogen uptake was ceased. After 22.5 hours, the reactor was cooled to room temperature and depressurized. LC analysis showed quantitative conversion of lysine. The catalyst was removed by filtration, washed with warm deionized water, and the filtrates were combined. The filtrate was treated with 50% aqueous NaOH (295-300 mL) until the pH reached 12.2. The resulting solution was concentrated under vacuum at 60-70° C. The resulting semi-solid was extracted first with ethanol and then with warm methanol. The extracts were combined and then concentrated on a rotary evaporator to yield crude lysinol (Lysinol-1.2a), as a yellow oil (346 g, 97% yield). Gas chromatography with flame ionization detection of crude Lysinol-1.2a showed 88 area % lysinol with smaller amounts of lighter components such as 2-hydroxymethylpiperidine The crude lysinol (Lysinol-1.2a) was vacuum distilled and the major fraction boiling at approximately 100-120° C. and $1.3 \times 10^{-5}$ MPa was collected to obtain lysinol (Lysinol-1.2) (260 g, 73% yield) as a colorless liquid with a faint amine odor. Gas chromatography analysis of Lysinol-1.2 showed lysinol in >99% purity. NMR (ppm, $D_2O$/trimethylpropane sulfonic acid sodium salt internal standard): $^{13}C\{^1\underline{H}\}$: 68.5 (C1), 54.0 (C2), 42.9 (C6), 34.8, 34.3 (C3, C5), 24.9 (C4). $^1$H, 3.50 (1H, dd, $^2J_{HH}$=11.0 Hz, $^3J_{HH}$=4.5 Hz), 3.33 (dd, $^2J_{HH}$=11.0 Hz, $^3J_{HH}$=7.0 Hz), 2.76 (1H, m), 2.58 (2H, t, J=6.8 Hz), 1.45-1.3 (4H, m), 1.3-1.2 (2H, m).

Example 1.3

Preparation of Lysinol (Lysinol-1.3) by Lysine Hydrogenation Using Phosphoric Acid at Higher Temperature A reactor was charged with 0.20 g (0.099 mmol Ru) Ru/C catalyst, 1.299 g (8.89 mmol) lysine, and 16.8 g of 1.0 M (0.0168 mol) $H_3PO_4$. After sealing, the reactor was pressure tested with nitrogen. The nitrogen was then vented and replaced with 4.1 MPa $H_2$ and the reactor was heated with stirring to 160° C. Upon reaching the target temperature, the pressure was increased to 6.9 MPa. The pressure dropped steadily over about 75 min to 6.4 MPa and then the rate of pressure drop began to slow After 180 min the pressure reached 6.1 MPa and $H_2$ was added to increase the pressure to 6.8 MPa. When the $H_2$ uptake had ceased, the reactor was cooled to room temperature. After venting the reactor, the slurry was filtered and the catalyst was washed with water. The water wash was combined with the filtrate. The water was removed on a rotary evaporator to give Lysinol-1.3, as a colorless syrup (3.088 g). LCMS of the Lysinol-1.3 showed lysinol as the major product (56 MS area %) and a minor amount of 2-hydroxymethyl piperidine (44 MS area %).
Measurement of Lysinol Enantiomeric Purity A sample of Lysinol (0.004 g, 0.03 mmol, 1 eq) was prepared according to the procedure of Example 1.2 using S-Lysine. The lysinol thus obtained was added to a glass vial with stir bar. Deuterated methylene chloride (Sigma Aldrich, 99% D Atom) (0.5 mL) was added further added to the Lysinol. Followed by addition of N,N-diisopropylethylamine (Sigma Aldrich, 99%) (0.01 mL, 0.06 mmol, 2 eq). The contents of the vial were stirred along with addition of S-Mosher chloride, i.e. [(S)-(+)-α-methoxy-α-(trifluoromethyl)phenylacetyl chloride] (Sigma Aldrich, 98% ee) (0.011 mL, 0.06 mmol, 2 equiv). Upon addition of S-Mosher chloride, some white cloudiness was observed in the solution but it dissipated after 5-10 min. The solution was stirred under inert atmosphere for 2 h and then diluted with 0.3 mL of deuterated methylene chloride and filtered through a 0.2 micron syringe filter into an NMR tube. Optionally at this point 1-2 drops of hexafluorobenzene (Sigma Aldrich, 99%) were added as a $^{19}$F chemical shift reference. $^{19}$F NMR was recorded at 376 MHz (400 MHz $^1$H) and 659 MHz (700 MHz $^1$H). To aid in the chemical shift assignments for the possible diastereomers these procedures were repeated with lysinol prepared by hydrogenation of enantiopure R-Lysine and racemic R,S-Lysine, both obtained from commercial sources (Sigma Aldrich), and by derivatization with (R)-(1)-α-methoxy-α-(trifluoromethyl)phenylacetyl chloride.

For the hydrogenation product of S-Lysine and S-Mosher chloride, two major peaks were observed in the $^{19}F\{^1H\}$ NMR at −71.36 ppm and −71.42 ppm. The singlet at −71.36 ppm corresponds to the fluorinated amide group located at the achiral C-6 position. The singlet at −71.42 ppm is assigned to the fluoroamide at the chiral C-2 position with S,S diastereoisomeric configuration. A smaller singlet observed at −71.33 ppm is assigned to the C-2 fluoroamide with R,S configuration. The relative amounts of S,S and R,S diastereomers were determined by both integration and peak deconvolution methods, and from these data the S-Lysinol was shown to have an enantiomeric purity of 95.2%, corresponding to 90.4% enantiomeric excess.

Example 2

Preparation of Lysinol Salt

The examples below illustrate the preparation of a 1:1 salt of lysinol with various diacids, useful for the preparation of high molecular weight polyamides.

Example 2.1

Of 1:1 Salt (Lysinol-HDA) of Lysinol with Adipic Acid (1,6 Hexanedioic Acid)

To a 1-neck 200 mL round bottom flask fitted with stir bar was added adipic acid (10.6 g, 0.073 mol) and absolute ethanol (81 mL). The flask was placed in a preheated 85° C. oil bath and was stirred until the solid was dissolved. Twice distilled lysinol (10.0 g, 0.076 mol) was then added dropwise to yield a white solid precipitate. After 5 minutes of stirring, the heat was removed and stirring was continued until the reaction had cooled to room temperature. The solid was filtered on a medium fritted funnel, rinsed with a small volume of ethanol, and was then dried under high vacuum overnight to get 19.7 g (97% yield) of lysinol salt with adipic acid (Lysinol-HDA), as a white solid having a melting point: 149-150° C. Elemental analysis for C12H26N2O5 resulted in close agreement with the calculated values as shown below:

| | C | H | N |
|---|---|---|---|
| Elemental Analysis of Lysinol-HDA | 51.76% | 9.69% | 10.02% |
| Calculated Composition of Lysinol-HDA | 51.78% | 9.42% | 10.06% |

Example 2.2

Preparation of 1:1 salt (Lysinol-DDDA) of Lysinol with 1,12-Dodecanedioic Acid

To a 20 mL scintillation vial was added 2.54 g (0.011 mol) of dodecanedioic acid, a stir bar, and 11 mL of absolute ethanol. The vial was heated in an 80° C. bath until the solid dissolved, and then the lysinol (1.52 g, 0.011 mol) was added dropwise with stirring. Approximately 15 minutes after removing the heat, a solid began to form. When cool, the entire sample solidified. The cake was broken up and was filtered on a medium frit, rinsing with a few mL of ethanol, giving a hygroscopic solid that was dried under high vacuum to get 2.85 g (71% yield) of lysinol salt with 1,12-dodecanedoic acid (Lysinol-DDDA), as a white solid having a melting point: 122-125° C. Elemental analysis for C18H38N2O5 resulted in close agreement with the calculated values as shown below:

| | C | H | N |
|---|---|---|---|
| Elemental Analysis of Lysinol-DDDA | 59.56% | 10.68% | 7.55% |
| Calculated Composition of Lysinol-DDDA | 59.64% | 10.57% | 7.73% |

Example 2.3

Preparation of 1:1 Salt of Lysinol (Lysinol-DDA) with Sebacic Acid (1,10 Decanedioic Acid)

To a scintillation vial was added 2.42 g (0.012 mol) of sebacic acid, a stir bar, and 11 mL of absolute ethanol. The vial was capped and was placed in an 80° C. block, where it was stirred until all of the solid dissolved. Lysinol (1.64 g, 0.012 mol) was then added dropwise. After removal from the heat, the reaction was stirred, becoming hazy after about 2 hours and completely solid by the next morning. The white solid was filtered on a medium fritted funnel and rinsed with a small portion of ethanol. It was dried on the under a stream of dry nitrogen to get 3.98 g (99% yield) of lysinol salt with sebacic acid (Lysinol-DDA), as a white solid having a melting point of 149-154° C. Elemental analysis for C16H34N2O5 resulted in close agreement with the calculated values as shown below:

|  | C | H | N |
|---|---|---|---|
| Elemental Analysis of Lysinol-DDA (average of two measurements) | 57.41% | 10.54% | 7.94% |
| Calculated Composition of Lysinol-HDA | 57.46% | 10.25% | 8.38% |

Example 2.4

Preparation of 1:1 Salt (Lysinol-BDA) of Lysinol with Succinic Acid (1,4-Butanedioic Acid)

To a scintillation vial was added 1.89 g (0.016 mol) of succinic acid, a stir bar, and 11 mL of absolute ethanol. The vial was capped and was placed in an 80° C. block reactor, and was stirred until the solid dissolved, after which time 2.2 g of lysinol (0.016 mol) was added dropwise and immediately precipitating a solid. The vial was slowly cooled to room temperature to yield the lysinol salt with sebacic acid (Lysinol-BDA), as a tacky semisolid.

Example 3.1

Preparation of Polyamide derived from Lysinol, (2,6 Diamino-1-Hexanol, (DAH)) and Adipic Acid (1,6 Hexanedioic Acid (HDA))

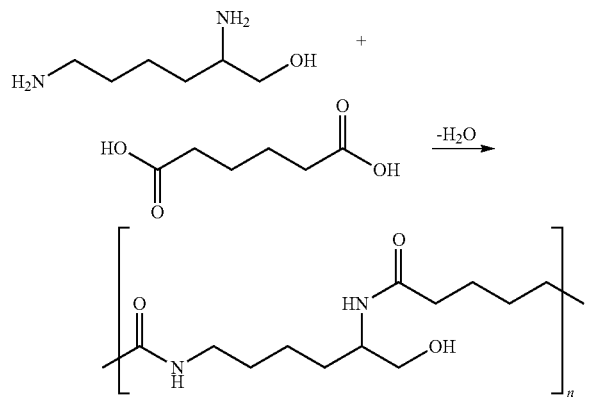

A glass-lined pressure reactor was charged with 2.85 g (0.0216 mol) of distilled lysinol, 3.15 g of adipic acid (0.0216 mol), and 4.0 g of deionized water. The reactor was purged with nitrogen and then pressurized to 0.34 MPa nitrogen. The reactor was occasionally vented or pressurized as needed during heating to maintain a pressure 1.7 MPa. Upon reaching 250° C. the needle valve was used to reduce the pressure to 0 MPa over a period of one hour while maintaining temperature at 250° C. When the gases were completely vented the reactor was cooled to room temperature and a yellow, tough lysinol derived polyamide DAH/HAD was obtained.

Example 3.2

Preparation of Polyamide Derived from 1:1 Salt of Lysinol (2,6 Diamino-1-Hexanol, (DAH)) and Adipic Acid (1,6 Hexanedioic Acid (HDA))

This example illustrates the polymer obtained from the 1:1 lysinol:adipic acid salt of Example 4.

The procedure described in Example 3.1 was followed using 1:1 lysinol:adipic acid salt (2.49 g, 0.00895 mol), as prepared in the Example 3.1 and deionized water (1.66 g). 2.12 g (98% yield) of yellow, tough lysinol derived polyamide DAH/HAD was recovered.

Example 4

Preparation of Copolymers of Lysinol (2,6 Diamino-1-Hexanol), Adipic Acid (1,6 Hexanedioic Acid) and 1,6-Diaminohexane Four stainless steel tubes, each 14 inch long and 1 inch diameter and capped on one end, were filled with adipic acid, 1,6-diaminohexane and lysinol in amounts given in Table 1 a for each of the 4 runs (Examples 4.1-4.4) to prepare about 25 grams of polymer in each tube. Each of the 4 tubes made a different composition of the Polyamide 66/lysinol 6 copolymer. The 66/lysinol 6 compositions were 95/5, 90/10, 85/15 and 80/20. Approximately 25 grams of water was added to each tube. Each tube was connected to its own pressure controller. The 4 tubes were initially heated in a sand bath to 130° C. at atmospheric pressure to purge air from the tubes with steam. The pressure controllers were set for 1.7 MPa and the tubes were heated to 250° C. over about 40 minutes. Before reaching 250° C. the tubes began venting steam. After reaching 250° C. the pressure in each of the tubes was reduced from 1.7 MPa to atmospheric pressure over 60 minutes, while increasing the temperature to 275° C. The tubes were heated for an additional 45 minutes at atmospheric pressure and at 275° C. before cooling. When the tubes were cool, they were opened and the polymer was removed. Table 4 shows the melting points of the 4 polymers obtained from 4 different runs. Melting point of Nylon 66 is shown for comparison in Table 2.

TABLE 1

| Example | Amount of Adipic Acid (g) | Amount of 78% 1,6-diaminohexane in water (HMD) (g) | Amount of Lysinol (g) | Amount of Water (g) |
|---|---|---|---|---|
| 4.1 | 16.09 | 15.78 | 0.73 | 25 |
| 4.2 | 16.03 | 14.91 | 1.45 | 25 |
| 4.3 | 15.98 | 14.04 | 2.17 | 25 |
| 4.4 | 15.92 | 13.18 | 2.88 | 25 |

TABLE 2

| Sample # | Mole % lysinol | Mole % HMD | Mn | Mw | Mz | PDI | $1^{st}$ mp, ° C. | $2^{nd}$ mp, ° C. |
|---|---|---|---|---|---|---|---|---|
| Example 4.1 | 5 | 95 | 22800 | 70330 | 502000 | 3.1 | 253 | 250 |
| Example 4.2 | 10 | 90 | 6704 | 1630 | 28450 | 2.4 | 244 | 236 |

TABLE 2-continued

| Sample # | Mole % lysinol | Mole % HMD | Mn | Mw | Mz | PDI | $1^{st}$ mp, °C. | $2^{nd}$ mp, °C. |
|---|---|---|---|---|---|---|---|---|
| Example 4.3 | 15 | 85 | | | | | 231 | 222 |
| Example 4.4 | 20 | 80 | | | | | 215 | 206 |
| Control-Nylon 66 | 0 | 100 | | | | | 264 | |

Example 5.1

Preparation of Lysinol-Epoxy Thermoset

This example illustrates the formation of an epoxy thermoset using an epoxy resin and lysinol as the amine hardener.

The epoxy resin, bisphenol A diglycidyl ether (BADGE, 1.03 g, 6.06 mmol epoxy groups), was combined with lysinol (0.196 g, 5.94 mmol amine groups) in an aluminum pan. The materials were warmed to 60° C. and mixed thoroughly with a wooden stick to give a colorless, transparent syrup. The viscosity rapidly increased and after 30 minutes a tough, clear, colorless tack-free solid lysinol Epoxy Thermoset corresponding to crosslinked structure 10 was obtained.

with lysinol in an aluminum pan in the proportions shown in the table 3. The materials were mixed thoroughly with a wooden stirrer to give a slightly opaque viscous liquid. The samples were remixed after 15 min at room temperature and then cured at 65° C. for 30 min to provide clear, colorless, tack-free solid Lysinol-Epoxy Thermosets.

Comparative Example A

Preparation of DETA-Epoxy Thermosets

For comparative purposes, the epoxy resin was combined with pure DETA as indicated in the table 3. The samples were mixed and cured for 30 min at 65° C. as described for the lysinol examples.

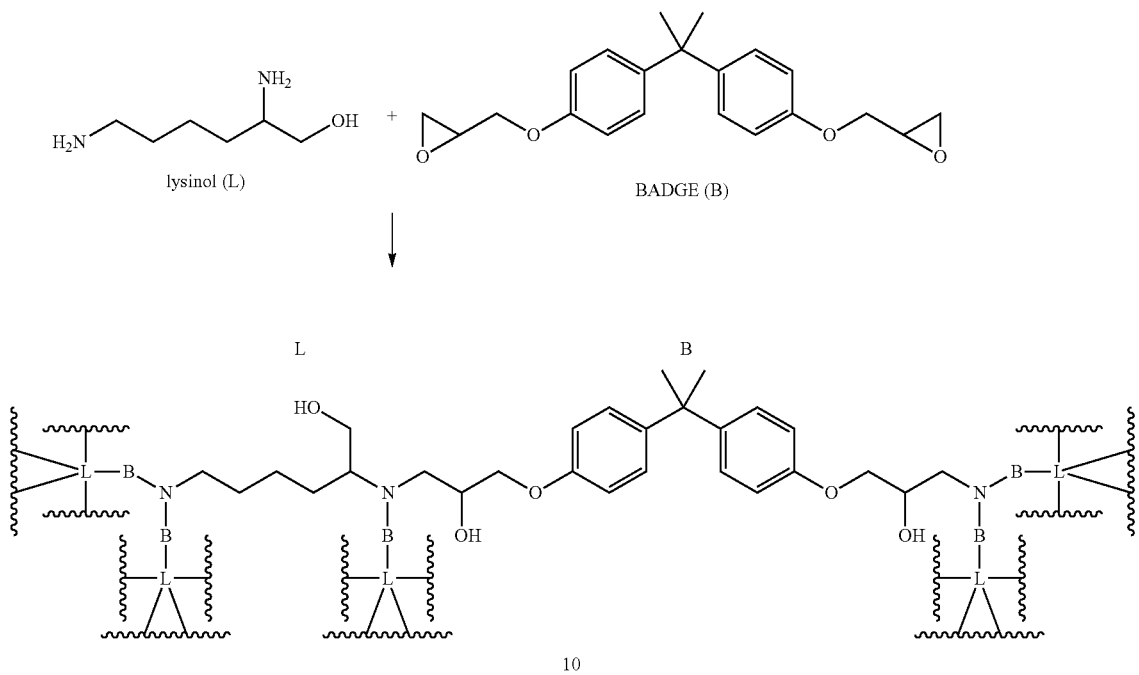

Example 5.2

Preparation of Lysinol-Epoxy Thermoset

This example illustrates that lysinol can replace common amine hardener active ingredient such as diethylenetriamine (DETA) in two part epoxy thermosets.

Loctite® Extra Time Epoxy, a two part dual syringe epoxy adhesive was obtained from Henkel Corporation (Rocky Hill, Conn.). The epoxy resin, a mixture of BADGE and its oligomers and polymers (Chemical Abstracts Registry Number 25068-38-6) was removed from the epoxy syringe and used for this example. The syringe containing the amine hardener, a mixture of a polyamide resin, amorphous silica, and DETA curing agent, was discarded. The epoxy resin was combined The lysinol examples (5.2-5.3) and the comparative examples (A.1-A.3) were found to be indistinguishable by visual inspection.

TABLE 3

| | BADGE Epoxy resin, grams | Lysinol, grams | $NH_2$ mmoles from Lysinol | DETA, grams | $NH_2$ mmoles from DETA |
|---|---|---|---|---|---|
| Example 5.2.1 | 1.11 | 0.196 | 2.97 | | |
| Example 5.2.2 | 1.04 | 0.293 | 4.44 | | |
| Example 5.2.3 | 0.99 | 0.382 | 5.79 | | |
| Example 5.2.4 | 8.88 | 1.56 | 47.2 | | |
| Comparative A.1 | 1.08 | | | 0.16 | 3.12 |

TABLE 3-continued

| | BADGE Epoxy resin, grams | Lysinol, grams | NH₂ mmoles from Lysinol | DETA, grams | NH₂ mmoles from DETA |
|---|---|---|---|---|---|
| Comparative A.2 | 0.99 | | | 0.22 | 4.28 |
| Comparative A.3 | 1.01 | | | 0.30 | 5.85 |
| Comparative A.4 | 6.48 | | | 0.642 | 31.1 |

Tensile Properties of Lysinol-Epoxy Thermoset (Example 5.2.4) & DETA-Epoxy Thermoset (Comparative Example A.4)

This example demonstrates that epoxy thermosets prepared using lysinol as the amine hardener have improved tensile properties compared to typical ethyleneamine hardeners, as shown in table 4.

A mixture of 8.88 g (26.1 mmol, 52.2 mmoles epoxy groups) of bisphenol A diglycidyl ether and 1.56 g (11.8 mmol, 47.2 mmol NH groups) lysinol was placed in molds conforming to an ASTM D1708-86 specimen die. Two samples (Example 5.2.4) were prepared and were cured overnight at room temperature and then at 65° C. for 30 minutes.

Similar procedure was used for the preparation of comparative sample DETA-Epoxy thermoset (A.4).

The tensile properties were then measured and are provided in Table 4.

TABLE 4

| Sample | Tensile modulus, Gpa | Tensile Strength, MPa | Strain at maximum Stress |
|---|---|---|---|
| Example 5.2.4 | 1.7 | 41 | 3.1% |
| Comparative Example A.4 | 1.4 | 34 | 2.8% |

Example 6

Preparation of Lysinol-Polyurea

Stoichiometry controls crosslink. This example illustrates the formation of a polyurea/polyurethane thermoset using lysinol as the crosslinking agent. Lysinol (1.008 g, 7.62 mmol) and diazabicylooctane (DABCO) (0.034 g) were combined in a plastic cup. Hexamethylene diisocyanate (HMDI, 1.94 g, 11.5 mmol) was added with stirring. A vigorous reaction with exotherm ensued immediately. Upon cooling to room temperature a pale yellow, tough lysinol-polyurea of structure 11 with urethane crosslinks of structure 12 was obtained.

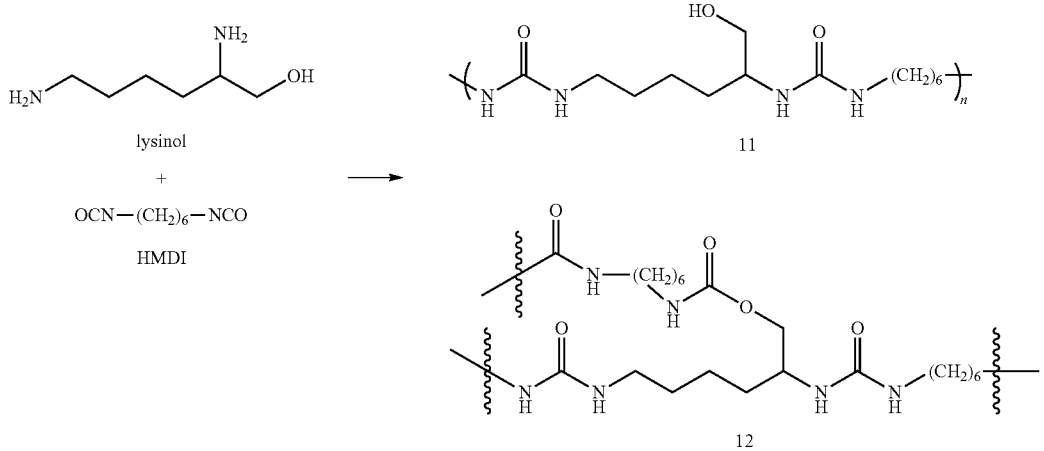

Example 7

Preparation of Lysinol-Polyurea Foam

This example illustrates the formation of a lysinol-polyurea foam comprising cross-linked polyurea formed using lysinol as the crosslinking agent.

Lysinol (1.058 g, 8.00 mmol), DABCO (0.017 g), surfactant Evonik Tegostab B8406 (0.025 g), and a foam expansion agent 1,1,1,4,4,4-hexafluoro-2-butene (cis-$CF_3CH$=$CHCF_3$) (0.337 g) were combined in a plastic cup to give an opaque solution. Hexamethylene diisocyanate (1.91 g, 11.3 mmol) was further added with stirring. A vigorous exothermic reaction and foaming ensued. A pale yellow, thermoset lysinol polyurea foam was obtained upon cooling to room temperature.

Example 8

Preparation of a Lysinol Poly(Amic Acid) and Polyimide

This example illustrates the copolymerization of lysinol and a dianhydride to give first a poly(amic acid) of structure 13 and subsequent conversion of that poly(amic acid) to a polyimide of structure 14 by the following reaction with BPDA:

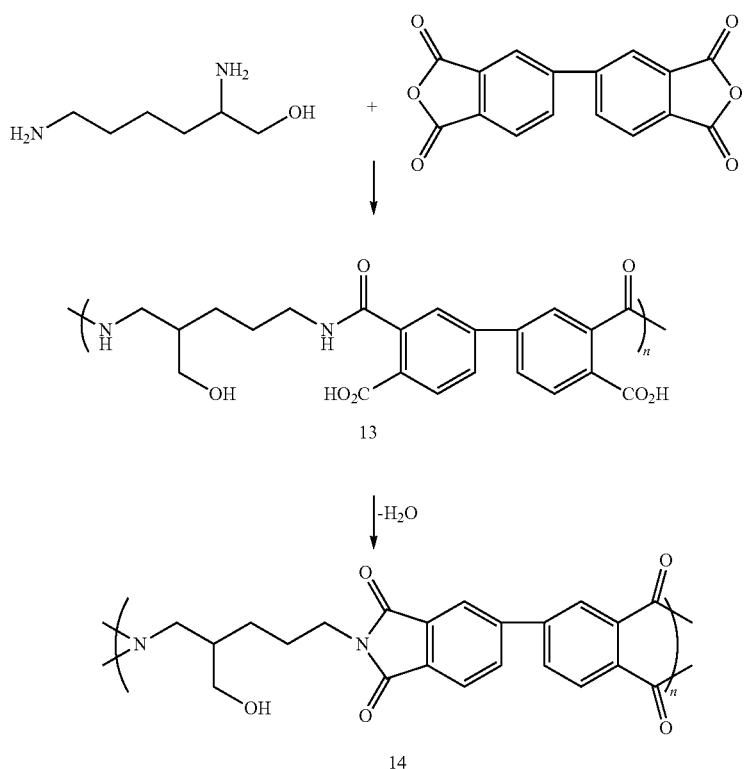

A flask was charged with lysinol (2.15 g, 0.016 mol) dissolved in 1-methyl-2-pyrrolidinone (NMP, 20 mL) and the solution was cooled to 0° C. A slurry of 3,3',4,4'-biphenyltetracarboxylic dianhydride (BPDA, 4.8 g, 0.016 mol) in 90 mL of NMP was added dropwise by pipette and while maintaining 0-5° C. solution temperature. The addition precipitated copious amounts of the poly(amic acid) as a colorless solid. When the addition was completed, the cold bath was removed and the reaction was permitted to warm to room temperature. As the temperature rose the precipitate dissolved to give a yellow solution. The solution was charged with 10 mL of o-xylene and the apparatus was fitted with a Dean Stark trap and a reflux condenser. The reaction was heated at 160° C. (interior temperature) for 4 hours, removing approximately 0.5 mL (theory is 0.58 mL for complete polyimide formation) of water. The dark yellow solution was added dropwise to 400 mL of stirring methanol to precipitate an off-white solid. The solid was filtered and suction dried to give 6.5 g (97% yield) polyimide. Infrared analysis (KBr) of the sample showed polyimide bands at 1774 cm$^{-1}$ and 1707 cm$^{-1}$ and a peak due to unconverted poly(amic acid) at 1655 cm$^{-1}$. The sample was heated at 180° C. under vacuum to complete conversion of the poly(amic acid) to polyimide, as evidenced by the loss of the 1655 cm$^{-1}$ band, and leaving only the polyimide bands at 1774 cm$^{-1}$ and 1707 cm$^{-1}$.

TGA of the final polyimide thus produced showed a decomposition temperature at 450-480° C. DSC showed a glass transition temperature (Tg) of 187° C.

COMPARATIVE EXAMPLES

Comparative Example B

Lysine Hydrogenation in the Absence of Acid

A reactor was charged with 1.03 g lysine, 7.5 mL deionized water, and 0.23 g of 5% Ru/C catalyst. The reactor was heated to 150° C. and brought to 6.9 MPa. After 1.3 h no gas uptake was observed and the experiment was halted. This experiment demonstrates that the presence of acid is required to hydrogenate lysine at the preferred pressures and temperatures of the present invention.

Comparative Example C

Hydrogenation of Lysine Methyl Ester as Described in Example 18 of Chinese Patent Application #CN102617364A This example replicates the hydrogenation of lysine methyl ester as described in the prior art CN102617364A and demonstrates that the procedure does not produce lysinol and instead provides substantial amounts of lysine and unreacted lysine methyl ester.

Lysine methyl ester (10.0 g, 0.0624 mol), 500 mL of deionized water, and 1.0 g of 50% slurry of Raney nickel 2800 in water were combined in a stainless steel autoclave. The reactor was pressurized with 6.0 MPa hydrogen (constant pressure) and heated to 60° C. for 6 hours, then cooled and vented to ambient temperature/pressure. The catalyst was removed by filtration over Celite with a small amount of decolorizing charcoal added. The filtrate was combined with filtrate from a replicate hydrogenation performed under exactly the same conditions. The combined filtrate from the two reactions was concentrated in vacuo at 55° C., to give 18.3 g of nearly colorless solid C1, consistent with the product description provided in CN102617364A Example 18. The solid C1 was washed with a mixture of ethanol and water and then vacuum dried, also as described in CN102617364A Example 18. The washings were combined and stripped under vacuum to yield a colorless solid C2.

Both C1 and C2 were analyzed by LCMS and NMR.

C1 was shown to be predominantly lysine. LCMS (ES+) showed the molecular ion for lysine (M+H=147), and a smaller peak for lysine methyl ester (M+H=161). $^{13}$C NMR ($D_2O/D_3PO_4$) showed two carbonyl (C=O) resonances in the 175-170 ppm range. Spiking C1 with authentic lysine and authentic lysine methyl ester showed the two peaks to be lysine (major) and lysine methyl ester (minor). As used herein, the term "authentic lysine" refers to as purchased lysine from Sigma-Aldrich, for example L-Lysine, >98%, Catalog number 62840.

Similarly, C2 was shown by LCMS and $^{13}$C NMR to be predominantly lysine methyl ester, containing minor amounts of lysine.

Neither C1 nor C2 showed detectable amounts of lysinol as compared to the authentic lysinol prepared by this invention or as described in the open literature.

Comparative Example D

Attempted Preparation of Lysinol by Hydrogenation of Lysine Ester as Described in Example 17 of Chinese Patent Application #CN102617364A This Comparative Example repeats Example 17 of CN102617364A but substitutes (S)-lysine for 3-methyl-2,3-di(aminomethyl)butyric acid and demonstrates the failure of that procedure to provide the desired hydrogenation product lysinol, and instead the recovery of unreacted (S)-lysine.

A high pressure reactor was charged with (S)-lysine (0.360 g, 0.0024 mol), 19.6 g of deionized water, Pd (palladium black from Strem Chemical Co., Catalogue number 46-1830, 0.020 g, 0.00018 mol), and a stir bar. The reactor was purged with nitrogen and then pressurized with 4.2 MPa of hydrogen and then heated. Upon reaching 120° C. the pressure was increased to 6.9 MPa with hydrogen. After 7 hours no gas uptake was observed. The reactor was cooled to room temperature and the catalyst was filtered and rinsed with deionized water. The filtrate was concentrated in vacuo at 50° C., giving 0.37 g of amorphous pale yellow foam D. Analysis ($^{13}$C-NMR, LC-MS) showed D to be unreacted lysine. In particular, $^{13}$C NMR shows the presence of the unreacted carboxylate group at ca. 180 ppm. No detectable amount of lysinol was observed by comparison with an authentic lysinol. Moreover, Examples 18 and 19 of CN102617364A describe lysinol as a white solid powder that can be recrystallized from ethanol/water mixtures. However, authentic lysinol is a liquid at room temperature and is completely miscible in both ethanol and water.

Comparative Examples E

Epoxy Hardener Application Using Lysinol and the Lysine Hydrogenation Product of CN102617364A Example 18

The following examples (E-1 through E-6) demonstrate the reactivity and product property differences between lysinol-1.2 prepared by the method of the present invention with those of the composition C1 or C2 obtained from the procedure described in CN102617356A Example 18 when used as hardeners with epoxy resins. The curing of epoxy resins is described in Example 34 of CN102617356A, however, the epoxy resin used in that Example is not disclosed in the published application. Therefore, for comparative purposes we chose to use bisphenol A diglycidyl ether (BADGE), a common epoxy resin used with amine hardeners.

The epoxy resin (BADGE, 1.03 g, 0.003 mol, 0.006 mol epoxide) was place in a 57 mm diameter aluminum weighing dish. It was briefly warmed on a 60° C. hot plate until it melted. Then, lysinol (0.196 g, 0.00148 mol, 0.00297 mol $NH_2$, 0.0059 mol NH) from Example 1.2 or from Comparative Example C(C1 or C2), was added and the mixture was thoroughly mixed with a wooden stick. The aluminum dish was placed in a 60° C. oven for 1 hour. Properties of the mixture obtained after cooling is summarized below in table 5.

TABLE 5

| Sample | As-prepared Lysinol | Properties of Final product obtained after mixing with BADGE and curing at 60° C. oven for 1 h |
|---|---|---|
| Control | Lysinol-1.2 | Hard, clear, and colorless thermoset |
| Comparative Example E.1 | C1 | Sticky heterogeneous fluid |
| Comparative Example E.2 | C2 | Sticky semisolid |

The table 5 shows that though curing at 60° C. for 1 h was sufficient for forming an epoxy thermoset from lysinol (Lysinol-1.2) prepared in accordance with the present invention, it was not sufficient time or temperature for products C1 & C2 obtained in accordance with the procedures described in the Example 18 of CN102617356A to form an epoxy thermoset.

Hence, the procedure was repeated with different curing conditions. Curing was done at 200° C. for 5 min in accordance with the procedure described in the Example 34 of CN102617356A. Table 6 summarizes the results of curing at higher temperature.

TABLE 6

| Sample | As-prepared Lysinol | Properties of Final product obtained after mixing with BADGE and curing at 200° C. oven for 5 min |
|---|---|---|
| Control | Lysinol-1.2 | Hard, clear, and colorless thermoset |
| Comparative Example E.3 | C1 | Thick sticky oil containing undissolved solid |
| Comparative Example E.4 | C2 | Dark brown, tack-free solid conatining large bubbles and solid heterogeneities |

The table 6 shows that a hard, clear and colorless epoxy thermoset was obtained from lysinol (Lysinol-1.2) prepared in accordance with the present invention upon curing at 200° C. for 5 min. However, product C1 failed to yield a thermoset under these curing conditions, while product C2 yielded a dark brown and heterogeneous thermoset.

It clearly demonstrates from the results tabulated in tables 5 and 6 that the Lysinol-1.2, prepared in accordance with the present invention has inherent chemical properties different from the products C1 and C2, prepared in accordance with the procedures described in the Example 18 of CN102617356A.

Comparative Examples F

Polyurea Preparation

Polymerization with 4,4'-Methylene di(phenylisocyanate) (MDI) Lysinol and the Lysine Hydrogenation Product from CN102617364A

Example 18

The following examples (F-1, F-2, F-3) demonstrate that polymer of MDI with lysinol (prepared in accordance with the present invention) has significantly different properties as compared to polymer of MDI and the products C1 or C2 (prepared as described in Example 18 of CN102617364A). The procedure as described in the Example 35 from CN102617364A was used to make the polymers.

Comparative Example F-1

Lysinol from Example 1.2

This example demonstrates that lysinol prepared by the method of the present invention upon reaction with a diisocyanate gives an insoluble, non-castable polymer.

To a 3-neck 100 mL round bottom flask fitted with a stir bar, condenser, thermocouple, and addition funnel, under nitrogen, was added lysinol (0.40 g, 0.003 mol), from Example 1.2 or from Comparative Example C(C1 or C2), and 25 g of anhydrous dimethylacetamide (DMAC). The solution was heated to 60-70° C., and 4,4'-methylene di(phenylisocyanate) (MDI, 1.37 g, 0.005 mol) was added in small portions, resulting in a 5-7° C. exotherm. After 10 minutes, the solution comprising Lysinol-1.2 had become a colorless, rubbery mass that was broken up with a spatula to facilitate mixing. After 30 minutes, a second portion of liquid lysinol (0.26 g, 0.002 mol) from Example 1.2 or from Comparative Example C(C1 or C2) in 12 g of DMAC was added dropwise over 10 minutes (total MDI: 5.47 mmol, 10.9 mmol NCO groups; total lysinol: 4.97 mmol, 9.94 mmol $NH_2$ groups; $NCO/NH_2$ mole ratio: 1.1). The reaction was stirred at 60-70° C. for an additional 2 hours, and was then cooled to room temperature, giving a product with properties dependent upon the starting material Lysinol-1.2 or product C1 or C2, as summarized in table 7 below:

TABLE 7

| Sample | As-prepared Lysinol | Properties of final product, polyurea |
|---|---|---|
| Control | Lysinol-1.2 | Colorless, rubbery mass that could not be poured or cast |
| Comparative Example E.1 | C1 | A soluble polymer that can be cast and dried to a hard film. (The final product obtained from starting material C1 or C2 was a homogeneous solution with viscosity comparable to pure DMAC. A small evaporating dish was charged with approximately 3 mL of the resulting solution. It was evaporated in a 60° C. oven under vacuum to give a hard, tack-free film.) |
| Comparative Example E.2 | C2 | |

Table 7 further supports that the Lysinol-1.2, prepared in accordance with the present invention has inherent chemical properties different from the products C1 and C2, prepared in accordance with the procedures described in the Example 18 of CN102617356A.

Comparison of Lysinol Prepared in Accordance with the Present Invention with Prior Art Syntheses.

Kihara et al. (Kihara, N.; Kushida, Y.; Endo, T.), *J. Polym. Sci.: Part A: Polym. Chem.* 1996, 34, 2173 (hereinafter, "Kihara") report preparation and characterization of (S)-lysinol. The synthesis employed in Kihara is a three step method beginning with (S)-lysine hydrochloride and involves protection of the nitrogen with benzoylcarbonyl groups, reduction of the carboxylic acid group with borane-THF, and removal of the nitrogen protecting groups to yield (S)-lysinol.

Kihara isolated and purified lysinol by vacuum distillation at 102.0-106.5° C. and 0.5 mm Hg, and described lysinol as a colorless oil at room temperature. This is in agreement with Lysinol prepared in accordance with the present invention, as illustrated in Examples 1.1-1.3, which was also a colorless oil that was purified by distillation at 90-123° C. and 0.2-0.3 mm Hg.

Kihara reported the proton NMR of lysinol in $d_6$-DMSO at 60 MHz, specifying resonances at δ 3.4-2.9 and integrating to two protons, δ 2.8-2.3 integrating to three protons, and δ 2.2-1.4 integrating to five protons, and δ 1.5-0.8 integrating to six protons. This data compares favorably with the proton NMR of our product recorded in $d_6$-DMSO, albeit at higher field (500 MHz): 3.3-3.1, two protons; 2.55, one proton; 2.45, two protons; 2.3-1.5, five protons (very broad); 1.5, broad and five protons; 1.05, one proton.

Kihara also reported the carbon NMR of lysinol in $d_6$-DMSO at 22.5 MHz. Kihara reported the following six resonances in the $^{13}$C NMR spectrum: δ 66.50, 52.81, 41.71, 33.74, 33.68, and 23.12. The lysinol prepared according to our procedure exhibits an identical $^{13}$C NMR spectrum in $d_6$-DMSO at 125.7 MHz, using the $d_6$-DMSO $^{13}$C resonance at δ 39.50 as a chemical shift reference: δ 66.57, 52.82, 41.72, 33.77, 33.71, 23.11.

In comparison, the colorless solid (C1) prepared according to Example 18 of CN102617364A, did not dissolve in $d_6$-DMSO and the NMR spectra could not be recorded, whereas the product C2 partially dissolved in $d_6$-DMSO. The proton and carbon NMR spectra contained no resonances assignable to lysinol as described above for lysinol prepared according to our procedure or to the procedure of Kihara. In addition to other unassigned resonances, resonances due to lysine methyl ester were observed. For example, the $^{13}$C NMR spectrum of this sample, recorded under identical conditions as described above ($d_6$-DMSO, 125.7 MHz), showed resonances with the following chemical shifts: δ171.61, 169.52, 52.67, 51.90, 51.47, 43.66, 38.00, 29.04, 28.25, 28.10, 26.62, 26.05, 25.91, 21.07. Anyone skilled in the art would recognize the resonances at δ 171.61 and 169.52 as most likely being due to C=O groups present in a carboxylic acid or ester groups, and inconsistent with the structure of lysinol.

What is claimed is:

1. A polyamide having the following structure:

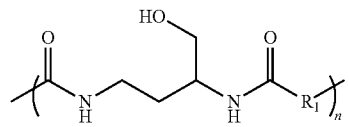

wherein $R^1$ is:
- a substituted or unsubstituted C1-C18 cyclic or acyclic alkyl group,
- a substituted or an unsubstituted aryl group comprising a single aromatic ring, multiple aromatic rings, or multiple condensed rings in which at least one is aromatic, or
- combinations thereof; and wherein the polyamide is derived from:
a. a diamine comprising lysinol and at least one of a dicarboxylic acid (HOOCR$^1$COOH), a dicarboxylic acid ester (R'OR$^1$OR'), a diacid halide (XOR$^1$OX), or a dinitrile (NCR$^1$CN); or
b. a salt comprising lysinol and a dicarboxylic acid (HOOCR$^1$COOH), wherein the molar ratio of lysinol and the dicarboxylic acid is 1:1.

2. The polyamide according to claim 1, wherein the lysinol is enantioenriched (S)-lysinol with a ratio of (S)-lysinol to (R)-lysinol in the range of 99:1 to 51:49.

3. The polyamide according to claim 2, wherein the polyamide is optically active.

4. The polyamide according to claim 1, wherein the dicarboxylic acid comprises oxalic acid; fumaric acid; maleic acid; succinic acid; glutaric acid; adipic acid; pimelic acid; suberic acid; azelaic acid; sebacic acid; itaconic acid; malonic acid; mesaconic acid dodecanediacid; 1,12-dodecanedioic acid; 1,14-tetradecanedioic acid; 1,16-hexadecanedioic acid; 1,18-octadecanedioic acid; 1,2- or 1,3-cyclohexane dicarboxylic acid; phthalic acid; isophthalic acid; p-(t-butyl)isophthalic acid; 1,2- or 1,3-phenylenediacetic acid; terephthalic acid; 2,5-dihydroxyterephthalic acid (DHTA); 4,4'-benzo-phenonedicarboxylic acid; 2,5 and 2,7-naphthalenedicarboxylic acid and mixtures thereof.

5. The polyamide according to claim 1, wherein the diacid halide comprises butylene diacid chloride; butylene diacid bromide; hexamethylene diacid chloride; hexamethylene diacid bromide; octamethylene diacid chloride; octamethylene diacid bromide; decamethylene diacid chloride; decamethylene diacid bromide; dodecamethylene diacid chloride; dodecamethylene diacid bromide; terephthaloyl dichloride; 4,4'-benzoyl dichloride; 2,6-naphthalenedicarboxyl acid dichloride; 1,5-naphthalene dicarboxyl acid dichloride; tolyl diacid chloride; tolylmethylene diacid bromide; isophorone diacid chloride; isophorone diacid bromide; 4,4'-methylenebis(phenyl acid chloride); 4,4'-methylenebis(phenyl acid bromide); 4,4'-methylenebis(cyclohexyl acid chloride); 4,4'-methylenebis(cyclohexyl acid bromide) and mixtures thereof.

6. The polyamide according to claim 1, wherein the dinitrile comprises methylglutaronitrile; ethylsuccino-nitrile; adiponitrile; fumarodinitrile; succinodinitrile; 3-hexenoic acid dinitrile; octanoic acid dinitrile; decanoic acid dinitrile; 1,5-dicyanopentane; 1,6-dicyanohexane; 1,7-dicyanoheptane; 1,8-dicyanooctane; 1,9-dicyanononane; 1,10-dicyanodecane; phthalonitrile; isophthalonitrile; terephthalonitrile; and mixtures thereof.

7. The polyamide according to claim 1, wherein the diamine further comprises a diamine comonomer and wherein the polyamide has the following general structure:

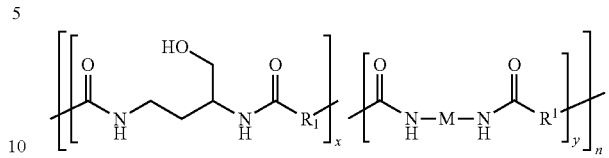

wherein M is a cyclic or acyclic aliphatic or aromatic group, where R$^1$ is a substituted or unsubstituted alkyl, aryl, or aralkyl group, and may be cyclic or acyclic;

wherein x can range from 1.0 to 0.01, y can range from 0 to 0.99, and x+y=1.0;

and wherein n is sufficiently large to provide an average molecular weight of at least 5,000 and preferably greater than 15,000.

8. The polyamide according to claim 7, wherein the diamine comonomer comprises 1,6-hexamethylenediamine; 1,5-pentamethylenediamine; 1,4-tetramethylenediamine; bis(aminomethyl)cyclohexane; 5-amino-1,3,3-trimethyl cyclohexanemethanamine; m-xylylenediamine; p-phenylenediamine; 3,3'-dimethylbenzidine; 2,6-naphthylenediamine; 4,4'-diaminodiphenyl ether; 4,4'-diaminodiphenyl sulfone; 1,12-dodecanediamine; and mixtures thereof.

9. The polyamide according to claim 1, further comprising partially cross-linked polyamide comprising amide and ester linkages wherein the crosslinked polymer has the following general structure:

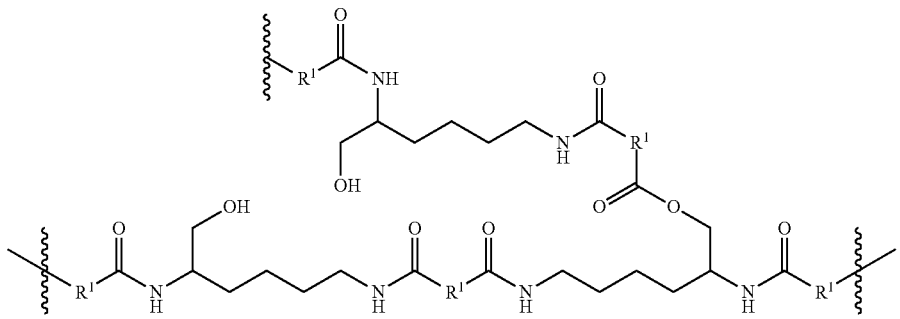

where R$^1$ is substituted or unsubstituted alkyl, aryl, or aralkyl group.

10. A salt comprising lysinol and a dicarboxylic acid, wherein the molar ratio of lysinol and the dicarboxylic acid is 1:1.

11. The salt according to claim 10, wherein the lysinol is enantiomerically enriched (S)-lysinol with a ratio of (S)-lysinol to (R)-lysinol in the range of 99:1 to 51:49.

12. The salt according to claim 10, wherein the dicarboxylic acid comprises oxalic acid; fumaric acid; maleic acid; succinic acid; glutaric acid; adipic acid; pimelic acid; suberic acid; azelaic acid; sebacic acid; itaconic acid; malonic acid; mesaconic acid dodecanediacid; 1,12-dodecanedioic acid; 1,14-tetradecanedioic acid; 1,16-hexadecanedioic acid; 1,18- octadecanedioic acid; 1,2- or 1,3-cyclohexane dicarboxylic acid; phthalic acid; isophthalic acid; p-(t-butyl)isophthalic acid; 1,2- or 1,3-phenylenediacetic acid; terephthalic acid; 2,5-dihydroxyterephthalic acid (DHTA); 4,4'-benzo-phenonedicarboxylic acid; 2,5 and 2,7-naphthalenedicarboxylic acid and mixtures thereof.

* * * * *